US012357690B2

(12) United States Patent
Choi et al.

(10) Patent No.: US 12,357,690 B2
(45) Date of Patent: Jul. 15, 2025

(54) EPITOPE OF EPB41L5, AND MONOCLONAL ANTIBODY

(71) Applicant: CELLASTER, Inc., Incheon (KR)

(72) Inventors: Kyung Chul Choi, Seoul (KR); Ho Geun Yoon, Goyang-si (KR); Jae Ho Cheong, Seoul (KR); Mi Hyeon Jeong, Jeonju-si (KR)

(73) Assignee: Cellaster, Inc., Incheon (KR)

( * ) Notice: Subject to any disclaimer, the term of this patent is extended or adjusted under 35 U.S.C. 154(b) by 355 days.

(21) Appl. No.: 17/265,755

(22) PCT Filed: Aug. 8, 2019

(86) PCT No.: PCT/KR2019/009960
§ 371 (c)(1),
(2) Date: Feb. 3, 2021

(87) PCT Pub. No.: WO2020/032614
PCT Pub. Date: Feb. 13, 2020

(65) Prior Publication Data
US 2021/0252145 A1    Aug. 19, 2021

(30) Foreign Application Priority Data

Aug. 9, 2018  (KR) ........................ 10-2018-0093045

(51) Int. Cl.
| A61K 39/395 | (2006.01) |
| A61K 39/00  | (2006.01) |
| A61P 35/00  | (2006.01) |
| C07K 16/18  | (2006.01) |
| C12N 15/113 | (2010.01) |
| G01N 33/574 | (2006.01) |

(52) U.S. Cl.
CPC .... *A61K 39/39558* (2013.01); *A61K 39/0011* (2013.01); *A61P 35/00* (2018.01); *C07K 16/18* (2013.01); *C12N 15/113* (2013.01); *G01N 33/574* (2013.01)

(58) Field of Classification Search
None
See application file for complete search history.

(56) References Cited

FOREIGN PATENT DOCUMENTS

| JP | 2015-021800 | 2/2015 |
| JP | 2017-108686 | 6/2017 |

OTHER PUBLICATIONS

Almagro & Fransson, Humanization of antibodies, Frontiers in Bioscience 2008; 13: 1619-33 (Year: 2008).*
Scott et al., Antibody therapy of cancer, Nature Review Cancer, 12, 278-287, Publication Date: Apr. 2012 (Year: 2012).*
English Translation of the International Search Report (ISR) for PCT/KR2019/009960 dated Nov. 25, 2019, pp. 1-3.
Hashimoto A. et al. "ZEB1 induces EPB41L5 in the cancer mesenchymal program that drives ARF6-based invasion, metastasis and drug resistance" Oncogenesis (2016) vol. 5, thesis No. e259, pp. 1-10.
Hashimoto, S. et al. "Lysophosphatidic acid activates Arf6 to promote the mesenchymal malignancy of renal cancer" Nature Communication (2016) vol. 7. thesis No. 10656, pp. 1-11.
NCBI, Reference Sequence No. NP_065960.2, band 4.1-like protein 5 isoform 1 (2018).
Altschul, Stephen F. et al. "Basic Local alignment search tool" J. Mol. Biol. (1990) vol. 215, pp. 403-410.
Chayen, Naomi E. "The role of oil in macromolecular crystallization" Structure (1997) vol. 5(10), pp. 1269-1274.
Chothia, Cyrus et al. "Canonical structures for the hypervariable regions o immunoglobulins" J. Mol. Biol. (1987) vol. 196, pp. 901-917.
Chothia, Cyrus et al. "Conformations of immunoglobulin hypervariable regions" Nature (1989) vol. 342, pp. 878-883.
Clackson, Tim et al. Making antibody fragments using phage display libraries Letters to Nature (1991) vol. 352, pp. 624-628.
Giege, R et al. The CCP4 suite: programs for protein crystallography (1994) Acta Cryst. (1994) vol. D50, pp. 760-763.
WorldCat entry, Elvin A. Kabat, Sequences of Proteins of Immunological Interest (1991).
Kohler et al. "Continuous cultures of fused cells secreting antibody of predefined specificity" Nature (1975) vol. 256, pp. 495-497.
Marks, James D. et al. "By-passing Immunization; Human antibodies from v-gene libraries displayed on Phage" J. Mol. Biol. (1991) vol. 222, pp. 581-597.
McPherson JR., Alexander "Crystallization of Proteins from Polyethylene Glycol" The Journal of Biological Chemistry (1976) vol. 251(20), pp. 6300-6303.
McPherson JR., Alexander "Current approaches to macromolecular crystallization" Eur. J. Biochem. (1990) vol. 189, pp. 1-23.
Needleman, Saul B. et al. "A General Method Applicable to the Search for Similarities in the Amino Acid Sequence of Two Proteins" J. Mol. Bio. (1970) vol. 48, pp. 443-453.
Pearson, William R. "Using the FASTA program to search protein and DNA sequence databases" Methods in Molecular Biology: Computer Analysis of Sequence Data (1994) vol. 24, pp. 307-331.
Chang et al., "YMO1 suppresses invasion and metastasis by inhibiting RhoC signaling and predicts favorable prognosis in hepatocellular carcinoma," Oncotarget, 7(34): 55585-600 (2016).
Huang et al., "Epithelial-mesenchymal transition in gastric cancer," The American Journal of Translational Research, 7(11): 2141-58 (2015).

(Continued)

*Primary Examiner* — Peter J Reddig
*Assistant Examiner* — Cheng Lu
(74) *Attorney, Agent, or Firm* — McDonnell Boehnen Hulbert & Berghoff LLP

(57) ABSTRACT

In the present disclosure, the effect of the TGFβ/Smad3/EPB41L5 molecular mechanism on cancer cells has been identified, and it has been found that high expression of EPB41L5 is correlated with poor overall survival of cancer patients, indicating that EPB41L5 is a potential prognostic marker of cancer. Thus, the present disclosure specifies an epitope of EPB41L5 to allow EPB41L5 to be recognized as an antigen, and relates to an antibody or a fragment thereof which binds specifically to the epitope. The antibody according to the present disclosure may be usefully employed as a therapeutic agent for EPB41L5-related cancer.

8 Claims, 27 Drawing Sheets

Specification includes a Sequence Listing.

(56) References Cited

OTHER PUBLICATIONS

Hirano et al., "EPB41L5 functions to post-transcriptionally regulate cadherin and integrin during epithelial-mesenchymal transition," The Journal of Cell Biology, 182(6): 1217-30 (2008).
Jeong et al., "EPB41L5 Mediates TGFβ-Induced Metastasis of Gastric Cancer," Clinical Cancer Research, 25(12): 3617-29 (2019).
Database Geneseq, "*Brucella* sp. B-cell epitope peptide, SEQ: 8097," EBI accession No. GSP:BBS16777, Database accession No. BBS16777 (2015).
Santa Cruz Biotechnology, "Anti-EPB41L5 Antibody (F-9): sc-515440" (2017), retrieved on Mar. 17, 2022 from URL: https://www.scbt.com/p/epb41l5-antibody-f-9?utm_campaign=genecards&utm_source=genecards.
Mak et al., "The Nature of Antigen—Antibody Interaction," The Immune Response, pp. 121-146 (2006).
Sela-Culang et al., "The structural basis of antibody-antigen recognition," Frontiers in Immunology, 4 (302), 1-13 (2013).

* cited by examiner

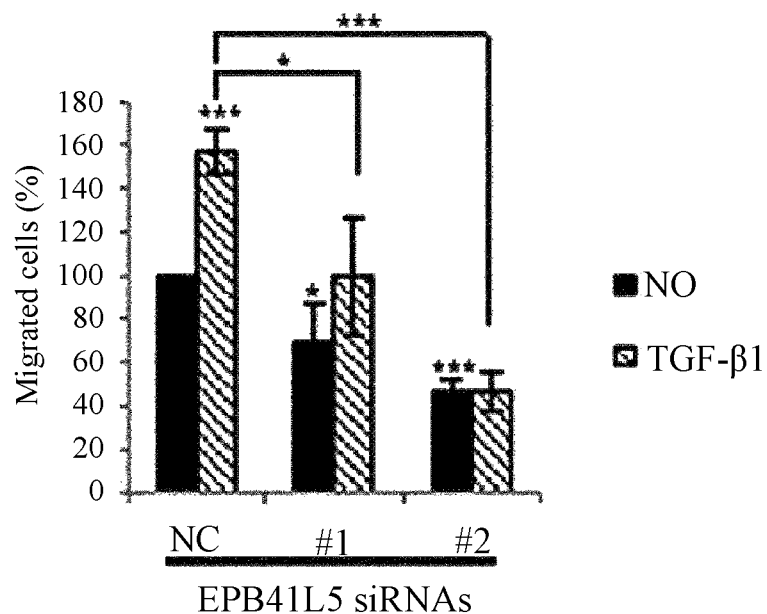
FIG. 5E
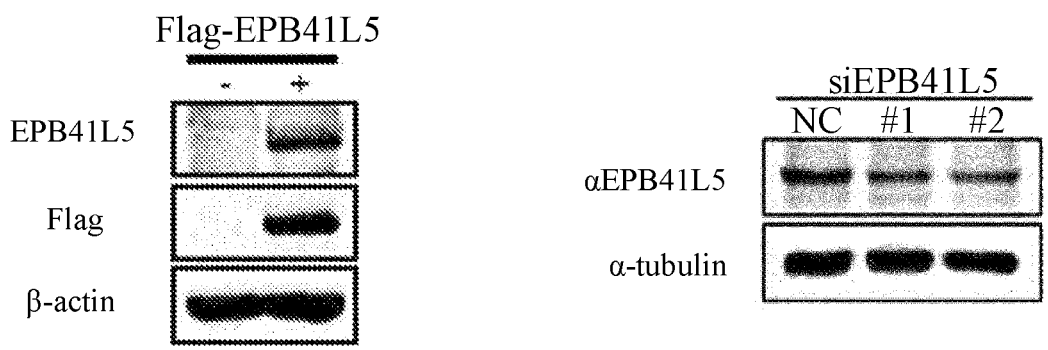
FIG. 6A
FIG. 6B

EPITOPE OF EPB41L5, AND MONOCLONAL ANTIBODY

CROSS-REFERENCE TO RELATED APPLICATIONS

This application is a U.S. National Stage entry of International Patent Application no. PCT/KR2019/09960, filed Aug. 8, 2019, which claims the benefit of priority of Korean Patent Application no. 10-2018-0093045, filed Aug. 9, 2018.

SEQUENCE LISTING STATEMENT

A computer readable form Sequence Listing is filed with this application by electronic submission and is incorporated into this application by reference in its entirety. The sequence listing submitted herewith is contained in the text file created May 19, 2023, entitled "21-0039-WO-US_SubstituteSequenceListing_ST25.txt" and is 16,384 bytes in size.

TECHNICAL FIELD

The disclosure relates to an epitope of EPB41L5 (Erythrocyte Membrane Protein Band 4.1 Like 5) protein and a monoclonal antibody that binds specifically thereto.

BACKGROUND ART

Cancer is a very fatal disease that can threaten the life of an individual by causing tissue cells to proliferate abnormally and unlimitedly to form a tumor that prevents the organ from performing its normal function. In 2017, the first leading cause of death in Korean was malignant neoplasm (cancer), and 27.6% of the total deaths were due to cancer.

Among cancer diseases, gastric cancer is one of the most major causes of death. In particular, metastatic gastric cancer is known as a malignant disease with a 5-year survival rate of less than 30% in the world. Although studies related to new biomarkers have been conducted for the treatment of such metastatic gastric cancer, the specific pathogenesis of the metastatic gastric cancer is not clearly known.

Targeted therapeutic agents developed to date include HER2-targeting therapeutic agents, VEGFR2-targeting therapeutic agents, and the like. In particular, Genetech/Roche found that HER2 is associated with a poor prognosis of breast cancer, ovarian cancer or gastric cancer, and thus Genetech/Roche developed a humanized monoclonal antibody (Herceptin or Trastuzumab) that binds to the extracellular domain of HER2/neu. In addition, Herceptin/Trastuzumab is a blockbuster drug that is currently sold worldwide, and recorded sales of $950 million in the United States only in the first half of 2011. However, Herceptin/Trastuzumab is known to have disadvantages in that it does not exhibit a clinical effect for other cancers that significantly overexpress HER2/neu, except for breast cancer, and in that patients who have received long-term administration of Herceptin/Trastuzumab have resistance to Herceptin/Trastuzumab.

Therefore, there are emerging needs to identify biomolecules related to cancer growth and metastasis and to discover biomarkers for new cancer-targeting therapies controlling cancer growth and metastasis by targeting these biomolecules.

The information disclosed in the above "Background Art" section are only for enhancement of understanding of the background of the present disclosure and should not be taken as an acknowledgement that this information forms a conventional art already known to a person skilled in the art.

DISCLOSURE

Technical Problem

An object of the present disclosure is to provide a 1- to 6-mer epitope selected from among the $619^{th}$ to $624^{h}$ amino acid residues of an EPB41L5 protein represented by the amino acid sequence of SEQ ID NO: 1.

Another object of the present disclosure is to provide a monoclonal antibody or a fragment thereof that recognizes the EPB41L5 protein represented by the amino acid sequence of SEQ ID NO: 1 as an antigen and binds specifically thereto.

Still another object of the present disclosure is to provide: a nucleic acid molecule encoding the monoclonal antibody or fragment thereof; and a vector comprising the nucleic acid molecule.

Yet another object of the present disclosure is to provide a vaccine composition for preventing or treating cancer, the composition containing, as an active ingredient: a 1- to 6-mer epitope selected from among the $619^{th}$ to $624^{th}$ amino acid residues of an EPB41L5 protein represented by the amino acid sequence of SEQ ID NO: 1; a nucleic acid molecule encoding the epitope; or a vector comprising the nucleic acid molecule.

A further object of the present disclosure is to provide a pharmaceutical composition for preventing, alleviating or treating cancer, the composition containing, as an active ingredient: the above-described monoclonal antibody or fragment thereof; a nucleic acid molecule encoding the same; or a vector comprising the nucleic acid molecule.

Further another object of the present disclosure is to provide a method of providing information for diagnosis of a disease caused by overexpression of EPB41L5.

Other objects and advantages of the present disclosure will be more clearly understood from the following detailed description of the present disclosure, the appended claims and the accompanying drawings.

Technical Solution

The present inventors have found that overexpression of EPB41L5 (Erythrocyte Membrane Protein Band 4.1 Like 5) protein compared to that in a normal control group is associated with cancer growth and metastasis, and have made extensive efforts to discover a biomarker for new cancer-targeting therapy capable of controlling cancer growth and metastasis by targeting the EPB41L5 protein. As a result, the present inventors have identified an epitope of EPB41L5 protein that inhibits cancer growth and metastasis through TGFβ-EPB41L5 signaling, thereby completing the present disclosure.

According to one aspect of the present disclosure, the present disclosure provides a 1- to 6-mer epitope selected from among the $619^{th}$ to $624^{th}$ amino acid residues of an EPB41L5 protein represented by the amino acid sequence of SEQ ID NO: 1.

In the present disclosure, the EPB41L5 protein may be represented by SEQ ID NO: 1, and information on the sequence thereof may be found in GenBank No. NM_020909.

In the present disclosure, the EPB41L5 (Erythrocyte membrane protein band 4.1 like 5) protein belongs to the NBL4 subgroup of the Erythrocyte Membrane Protein Band 4.1 superfamily, which has an FERM domain at the N-terminus and a non-homologous sequence at the C-terminus.

In the present specification, the term "epitope" refers to a localized region of an antigen to which an antibody or a fragment thereof may specifically bind. Epitopes usually consist of surface groups of molecules such as amino acids or sugar side chains, and usually have specific three-dimensional structural characteristics, as well as specific charge characteristics. Conformational and non-conformational epitopes are distinguished in that the binding to the conformational epitope but not the non-conformational epitope is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specific antigen binding peptide (that is, the amino acid residue is within the footprint of the specific antigen binding peptide).

In the present disclosure, the epitope may comprise any one or more amino acids selected from among the amino acid residues at positions 619, 620, 621, 622, 623 and 624 of the EPB41L5 protein.

In the present disclosure, the epitope may consist of the $619^{th}$ to $624^{th}$ amino acids of the EPB41L5 protein, and may preferably consist of an amino acid sequence represented by SEQ ID NO: 2, but is not limited thereto.

In the present disclosure, the epitope containing the amino acids at the above-described positions, when used as a vaccine or composition, may be used in combination with a carrier so that the structure thereof is maintained. Although the carrier according to the present disclosure is not particularly limited, as long as it is biocompatible and may achieve the desired effect in the present disclosure, it may preferably be selected from among peptides, serum albumin, immunoglobulins, hemocyanin, and polysaccharides.

According to another aspect of the present disclosure, the present disclosure provides a monoclonal antibody or a fragment thereof that recognizes the EPB41L5 protein represented by SEQ ID NO: 1 as an antigen and binds specifically thereto.

According to a preferred embodiment of the present disclosure, the antibody or fragment thereof according to the present disclosure may bind to a 1- to 6-mer epitope selected from among the $619^{th}$ to $624^{th}$ amino acids of EPB41L5 protein.

Epithelial-mesenchymal transition (EMT) is a primary cause of gastric cancer metastasis, and many studies have reported that the TGFβ signaling regulates epithelial-mesenchymal transition. TGFβ ligand binds to TGFβ receptor I through the serine/threonine kinase TGFβ receptor II. The TGFβ receptor dimer is activated by the phosphorylation of Smad2/3 and, in turn, the phosphorylated Smad2/3 binds to the co-Smad Smad4, and this protein complex enters the nucleus and regulates epithelial-mesenchymal transition-related genes such as PAI-1, ZEB1, Slug, and like. Some studies reported that TGF-β1 expression is enhanced in the mucosa, serum and tissue of gastric cancer patients, and that high expression of TGF-β1 is involved in the low survival rate of gastric cancer patients.

In the present disclosure, it was confirmed through oligonucleotide microarray analysis and Kaplan-Meier survival analysis that the survival rate of cancer patients was low when the expression levels of EPB41L5 gene and a protein encoded thereby were high. In addition, it was confirmed that EPB41L5 mRNA and protein expressions in four gastric cancer cell lines (KATOIII, MKN28, SNU1, and SNU719) were increased by TGF-β1, and that the increased EPB41L5 expression induced by TGF-β1 was regulated by Smad-dependent TGFβ signaling. The increased EPB41L5 protein expression induced by TGFβ signaling may affect cancer metastasis by interaction with the cell adhesion molecule p120-catenin. Accordingly, the monoclonal antibody or fragment thereof according to the present disclosure binds specifically to an epitope that is an amino acid sequence which is bound when an EPB41L5/p120-catenin complex is formed, and thus the monoclonal antibody or fragment thereof may very effectively inhibit cancer occurrence, metastasis or growth by effectively inhibiting the formation of the EPB41L5/p120-catenin complex.

According to a preferred embodiment of the present disclosure, the monoclonal antibody and fragment thereof binds specifically to EPB41L5 represented by SEQ ID NO: 1 and blocks the interaction between EPB41L5 and p120-catenin. Although the monoclonal antibody and fragment thereof is not particularly limited to as long as it is produced using the EPB41L5 protein represented by SEQ ID NO: 1 as an antigen, it is most preferably produced using the amino acid sequence of SEQ ID NO: 2 as an antigen, but is not limited thereto.

In the present specification, the term "epitope" refers to a localized region of an antigen to which an antibody or a fragment thereof may specifically bind. An epitope may be, for example, contiguous amino acids of a polypeptide as an antigen, or an epitope may come together from two or more non-contiguous regions juxtaposed by tertiary folding in a polypeptide. An epitope may comprise at least 2, at least 3, at least 4, at least 5, at least 6, at least 7, at least 8, at least 9, at least 10, at least 11, at least 12, at least 13, at least 14 or at least 15 contiguous or non-contiguous amino acids in the unique three-dimensional structure of the antigen. The antibody or fragment thereof according to the present disclosure recognizes EPB41L5 as an antigen and binds specifically thereto. Specifically, the antibody or fragment thereof may specifically bind to a 1- to 6-mer epitope selected from among the 619* to 624* amino acid residues of EPB41L5, and the epitope may comprise one or more amino acids.

Methods for determining an epitope to which a given antibody binds (e.g., epitope mapping) include various methods such as immunoblotting and immunoprecipitation assays based on antibody reactivity tests. The three-dimensional spatial structure of the epitope may be determined using various methods such as x-ray crystallography, 2-dimensional nuclear magnetic resonance and HDX-MS (Epitope Mapping Protocols in Methods in Molecular Biology, Vol. 66, G. E. Morris, Ed. (1996)).

According to a preferred embodiment of the present disclosure, an epitope to which the antibody or fragment thereof according to the present disclosure may bind may be determined by NMR spectroscopy, X-ray diffraction crystallography, ELISA assay, HDX-MS (hydrogen/deuterium exchange coupled with mass spectrometry), array-based oligo-peptide scanning assays, and/or mutagenesis mapping (Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303).

As used herein, the term "antibody" may be any type of antibody (e.g., IgG, IgE, IgM, IgD, IgA, or IgY) among immunoglobulin molecules, or may be any isotype of antibody (e.g., IgG1, IgG2, IgG3, and IgG4 in humans; and IgG1, IgG2a, IgG2b, and IgG3 in mice). Immunoglobulins (e.g., IgG1) may exist in several allotypes, and the term "antibody" as used herein includes generally known isotypes and allotypes. In addition, the term "antibody" as used herein may be IgG1, IgG2, IgG3, IgG4, or a hybrid thereof (e.g., a hybrid of IgG2 and IgG4).

As used herein, the term "monoclonal antibody" refers to an antibody that displays single binding specificity and affinity for a particular epitope.

The monoclonal antibody of the present disclosure may be produced, for example, by the hybridoma method first described in Kohler et al., Nature 256, 495 (1975), or by a recombinant DNA method. In addition, the monoclonal antibody may be isolated from a phage antibody library using, for example, techniques described in Clackson et al., Nature 352, 624-628 (1991) and Marks et al., J. Mol. Biol. 222, 581-597 (1991). Monoclonal antibodies may be obtained from any suitable source. The monoclonal antibody in the present disclosure may be obtained from hybridomas produced either from cells expressing EPB41L5 antigen or from cells obtained from mice immunized with the antigen of interest in the form of a nucleic acid encoding EPB41L5 antigen. The monoclonal antibody may also be obtained from hybridomas derived from antibody-expressing cells of immunized humans or non-human mammals such as rats, dogs, primates, and the like.

In the present specification, the monoclonal antibody is used in the sense of including a fragment thereof, and the fragment preferably refers to an antigen-binding fragment. The fragment may be produced using various methods known in the art. For example, Fab and F(ab')2 fragments may be produced by proteolytic cleavage of immunoglobulin molecules using enzymes such as papain (production of Fab fragment) or pepsin (production of (F(ab')2) fragment).

As used herein, the term "fragment" may be Fab, Fab', F(ab')2, Fv, scFV (single chain Fv), or sdAb containing a monomeric VH or VL domain, and the fragment is well known in the art.

In the present disclosure, the antibody may be, but is not limited to, a chimeric antibody, a humanized antibody, a bivalent-bispecific molecule, a minibody, a domain antibody, a bispecific antibody, an antibody mimic, a diabody, a triabody, a tetrabody, or a fragment thereof.

In the present disclosure, the "chimeric antibody" is an antibody obtained by recombining the variable region of a mouse antibody and the constant region of a human antibody, and has a significantly improved immunity compared to the mouse antibody.

In addition, in the present disclosure, the "humanized antibody" refers to an antibody obtained by modifying the protein sequence of an antibody, derived from a non-human species, so as to be similar to that of an antibody variant naturally produced in humans. For example, the humanized antibody may be produced by recombining a mouse-derived CDR with a human antibody-derived FR to produce a humanized variable region and recombining the same with a desired human antibody constant region.

The monoclonal antibody or fragment thereof according to the present disclosure inhibits physiological effects associated with the growth and metastasis of cancer mediated by the EPB41L5 gene or the protein encoded thereby. Specifically, increased TGF-β1 expression in cancer is identified and the expression level of the EPB41L5 protein is increased by TGF-β1, but the expression level of the EPB41L5 protein is regulated by Smad-dependent TGFβ signaling. That is, increased EPB41L5 protein expression level induced by TGF-β1 affects the migration and invasion of cancer through epithelial-mesenchymal transition, and cell signaling mediated by the EPB41L5 protein may be very effectively inhibited by treatment with the monoclonal antibody or fragment thereof including the above-described antigen-binding protein.

As used herein, the expression "inhibit growth" is intended to include any measurable decrease in cell growth when contacted with the monoclonal antibody or fragment thereof, as compared to the growth of the same cells not in contact with the monoclonal antibody or fragment thereof of the present disclosure, for example, an inhibition of growth of a cell culture by about 10%, 20%, 30%, 40%, 50%, 60%, 70%, 80%, 90%, or 100%. The decrease in cell growth may be caused by various mechanisms.

The monoclonal antibody or fragment thereof contains one or more CDRs (e.g., 1, 2, 3, 4, 5 or 6 CDRs). The monoclonal antibody or fragment thereof, which binds to the EPB41L5 protein as an antigen, is a polypeptide containing one or more complementarity-determining regions (CDRs) as described herein. In the antigen binding protein, the CDRs are oriented such that the proper antigen binding properties of the CDR(s) are achieved. In general, the antigen binding protein that is provided herein may interfere with, block, reduce or modulate the interaction between EPB41L5 and p120-catenin. That is, the antigen binding protein may inhibit TGF-β1-mediated cancer metastasis and growth by inhibiting the formation of the EPB41L5/p120-catenin complex in a subject.

In the present disclosure, the monoclonal antibody or fragment thereof may comprise, but is not limited to:
 a heavy-chain variable region comprising a heavy-chain CDR1 represented by SEQ ID NO: 6, a heavy-chain CDR2 represented by SEQ ID NO: 7, and a heavy-chain CDR3 represented by SEQ ID NO: 8; and a light-chain variable region comprising a light-chain CDR1 represented by SEQ ID NO: 9, a light-chain CDR2 represented by SEQ ID NO: 10, and a light-chain CDR3 represented by SEQ ID NO: 11.

In the present disclosure, the monoclonal antibody or fragment thereof may comprise, but is not limited to:
 a heavy-chain variable region represented by SEQ ID NO: 12; and a light-chain variable region represented by SEQ ID NO: 13.

A VH domain or one or more CDRs thereof may be linked to a constant domain for forming a heavy chain. Similarly, a VL domain or one or more CDRs thereof may be linked to a constant domain for forming a light chain. A full-length heavy chain and a full-length light chain combine to form a full-length antibody.

In the present disclosure, as described above, the monoclonal antibody or fragment thereof, which binds to a 1- to 6-mer epitope selected from among the $619^h$ to $624^{th}$ amino acid residues of the EPB41L5 protein represented by SEQ ID NO: 1, binds specifically to the EPB41L5 represented by SEQ ID NO: 1, thereby exhibiting an effect of blocking the interaction between EPB41L5 and p120-catenin.

In the present disclosure, the monoclonal antibody or fragment thereof may be used for therapeutic applications. Specifically, it may inhibit, suppress or modulate one or more biological activities of the EPB41L5 gene or the protein encoded thereby, and may bind specifically to the EPB41L5 protein, thereby substantially inhibiting EPB41L5 protein-induced cell signaling through competitive binding with a protein (e.g., TGF-β1) that may bind to the EPB41L5 protein. Thus, the monoclonal antibody or fragment thereof may be very effectively used for therapeutic applications.

Variable regions of immunoglobulin chains generally exhibit the same overall structure comprising relatively conserved framework regions (FR) joined by three hypervariable regions (more often called "complementarity determining regions" or CDRs). The CDRs from the two chains of each heavy chain/light chain pair mentioned above are typically aligned by the framework regions to form a structure that binds specifically to a specific epitope on the target protein (e.g., PCSK9). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD)], or [Chothia & Lesk, 1987, J. Mol. Biol. 196:901-917]; [Chothia et al., 1989, Nature 342:878-883.

Various heavy chain and light chain variable regions may be provided herein, and as described above, each of these variable regions may be attached to the above heavy and light chain constant regions to form a complete antibody heavy and light chain, respectively. Furthermore, each of the formed heavy and light chain sequences may be combined to form a complete antibody structure.

The monoclonal antibody or fragment thereof according to the present disclosure may include a variant of the amino acid sequence, as long as it may bind specifically to the EPB41L5. For example, the amino acid sequence of the antibody may be modified to improve the binding affinity and/or other biological properties of the antibody. Such modifications include, for example, deletion, insertion and/or substitution of one or more residues in the amino acid sequence of the antibody.

Such amino acid variations are based on the relative similarity of the amino acid side-chain substituents, for example, their hydrophobicity, hydrophilicity, charge, size, and the like. An analysis of the size, shape and type of the amino acid side-chain substituents reveals that arginine, lysine, and histidine are all positively charged residues; that alanine, glycine and serine are all of a similar size; and that phenylalanine, tryptophan and tyrosine all have a similar shape. Therefore, based upon these considerations, arginine, lysine and histidine; alanine, glycine and serine; and phenylalanine, tryptophan and tyrosine; may be defined as biologically functional equivalents.

To introduce variations, the hydropathic index of amino acids may be considered. Each amino acid has been assigned a hydropathic index on the basis of their hydrophobicity and charge characteristics, which are as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art. It is known that certain amino acids may be substituted for another amino acids having a similar hydropathic index and still retain a similar biological activity. To introduce variations based on the hydropathic index, substitutions are made between amino acids that exhibit a hydropathic index difference of preferably within ±2, more preferably ±1, even more preferably ±0.5.

Meanwhile, it is also known that substitution between amino acids having similar hydrophilicity values results in proteins having equivalent biological activity. As disclosed in U.S. Pat. No. 4,554,101, the following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). To introduce variations based on the hydropathic value, substitutions are made between amino acids that exhibit a hydropathic value difference of preferably within +2, more preferably +1, even more preferably +0.5.

Amino acid exchanges in proteins, which do not generally alter the activity of molecules, are known in the art (H. Neurath, R. L. Hill, The Proteins, Academic Press, New York (1979)). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, and Gln/Glu.

Considering the above-described variations having biologically equivalent activity, it is interpreted that the binding molecules of the present disclosure also include a sequence showing substantial identity with the sequence set forth in the Sequence Listing.

As used herein, the term "substantial identity" means a sequence showing at least 61% homology, more preferably 70% homology, even more preferably 80% homology, most preferably 90% homology, as determined by aligning the sequence of the present disclosure with any other sequence to correspond to each other as much as possible and analyzing the aligned sequence using an algorithm commonly used in the art. Alignment methods for sequence comparison are known in the art. Various methods and algorithms for alignment are disclosed in Smith and Waterman, Adv. Appl. Math. 2:482(1981); Needleman and Wunsch, J. Mol. Bio. 48:443(1970); Pearson and Lipman, Methods in Mol. Biol. 24: 307-31(1988); Higgins and Sharp, Gene 73:237-44 (1988); Higgins and Sharp, CABIOS 5:151-3(1989); Corpet et al., Nuc. Acids Res. 16:10881-90(1988); Huang et al., Comp. Appl. BioSci. 8:155-65(1992) and Pearson et al., Meth. Mol. Biol. 24:307-31(1994). NCBI Basic Local Alignment Search Tool (BLAST) (Altschul et al., J. Mol. Biol. 215:403-10(1990)) is available from NCBI (National Center for Biological Information), and may be used in conjunction with sequencing programs, such as blastp, blasm, blastx, tblastn and tblastx, on the Internet. Sequence homology comparison methods using BLAST.

In the present disclosure, although the binding molecule, preferably the antibody, may be produced by a conventional method for producing an antibody, it may be produced by affinity maturation.

As used herein, the term "affinity maturation" refers to a process in which antibodies having increased affinity for an antigen are produced by activated B cells in the course of an immune response. For the purpose of the present disclosure, the affinity maturation allows antibodies or antibody fragments to be produced due to affinity maturation based on the principles of mutation and selection, in the same process that occurs in nature.

According to still another aspect of the present disclosure, the present disclosure provides: a nucleic acid molecule encoding the monoclonal antibody or fragment thereof; a vector comprising the nucleic acid molecule; and a host cell comprising the vector.

The nucleic acid molecule of the present disclosure may be an isolated or recombinant nucleic acid molecule. Examples of such nucleic acid molecules include single- and double-stranded DNA and RNA and their corresponding complementary sequences. The "isolated nucleic acid" may be isolated from a naturally occurring source. In this case, the isolated nucleic acid is separated from the peripheral gene sequence present in the genome of a subject from which the nucleic acid was isolated. The isolated nucleic acid may be understood as a nucleic acid, for example, a PCR product, a cDNA molecule or an oligonucleotide, which is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence, or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancers does not located adjacent. The linkage is performed by ligation at a convenient restriction enzyme site. In the case where this site does not exist, a synthetic oligonucleotide adaptor or a linker is used according to a conventional method.

As used herein, the term "vector" refers to a carrier into which a nucleic acid sequence can be inserted for introduction into a cell where it can be replicated. The nucleic acid sequence can be exogenous or heterologous.

As used herein, the term "expression vector" refers to a vector containing a nucleic acid sequence encoding at least a portion of a gene product capable of being transcribed. In some cases, RNA molecules are then translated into a protein, polypeptide, or peptide. Expression vectors may contain a variety of control sequences. In addition to control sequences that regulate transcription and translation, vectors and expression vectors may contain nucleic acid sequences that provide other functions as well.

In a specific embodiment of the present disclosure, the expression vector may be selected from the group consisting of a commercially widely available pCDNA vector, F, R1, RP1, Col, pBR322, ToL, Ti vector; cosmids; phages such as lambda, lambdoid, M13, Mu, p1, P22, Qµ, T-even, T2, T3, T7, etc.; and plant viruses, but is not limited thereto. Any expression vector known to those skilled in the art may be used in the present disclosure, and the choice of the expression vector is dependent on the nature of the host cell of choice. Introduction of the vector into host cells can be effected by, but not limited to, calcium phosphate transfection, virus infection, DEAE-dextran mediated transfection, lipofectamin transfection or electroporation, and any person skilled in the art can select and use an introduction method suitable for the expression vector and host cell used. Preferably, the vector contains one or more selectable markers, but is not limited thereto, and a vector containing no selectable marker may also be used to determine whether a product has been produced. The choice of the selectable marker may depend on the host cells of choice, and the present disclosure is not limited thereto because this choice is performed using a method already known to those skilled in the art.

To facilitate the purification of the nucleic acid molecule of the present disclosure, a tag sequence may be inserted and fused into the expression vector. Examples of the tag include, but are not limited to, a hexa-histidine tag, a hemagglutinin tag, a myc tag or a flag tag. Any tag facilitating purification, known to those skilled in the art, may be used in the present disclosure.

As used herein, the term "host cell" includes eukaryotes and prokaryotes, and refers to any transformable organism that is capable of replicating the vector or expressing the gene encoded by the vector. The host cell may be transfected or transformed by the vector. The transfection or transformation refers to a process in which the exogenous nucleic acid molecule is transferred or introduced into the host cell.

Preferred examples of the host cell of the present disclosure include, but are not limited to, bacterial cells, CHO cells, HeLa cells, HEK293 cells, BHK-21 cells, COS7 cells, COP5 cells, A549 cells, NIH3T3 cells, etc.

According to yet another aspect of the present disclosure, the present disclosure provides a vaccine composition for preventing or treating cancer, the vaccine composition containing, as an active ingredient: a 1- to 6-mer epitope selected from among the $619^{th}$ to $624^{th}$ amino acid residues of an EPB41L5 protein represented by the amino acid sequence of SEQ ID NO: 1; a nucleic acid molecule encoding the same; or a vector comprising the same.

In the vaccine composition of the present disclosure, the contents related to the EPB41L5, epitope, nucleic acid molecule and vector are the same as described above, and thus description thereof is omitted to avoid excessive complexity of the present specification.

The vaccine may be a live vaccine, an attenuated vaccine or an inactivated vaccine, and the vaccine may be used as a feed or feed additive.

The vaccine composition of the present disclosure can prevent or treat cancer by inducing an immune response as well as a systemic immune response to EPB41L5 through active immunity. Active immunity means that, when a pathogen invades, a living body is immunized by generating antibodies in its own body.

In addition, the vaccine composition of the present disclosure may be used to prevent or treat cancer by administering the same to a subject.

The cancer in the present disclosure may be a cancer in which the EPB41L5 gene or the protein encoded thereby is determined to be overexpressed.

As used herein, the term "overexpression" means that the expression level of the EPB41L5 gene or the protein encoded thereby is 1.1 to 2 times higher than that in control cells (e.g., normal cells of the organ of interest) when the expression level of EPB41L5 is measured by an appropriate expression assay. The kind of the cancer in the present disclosure is not limited, and the vaccine composition of the present disclosure may be administered to treat a number of cancers, including lymphomas such as leukemia, acute lymphocytic leukemia, acute nonlymphocytic leukemia, chronic lymphocytic leukemia, chronic myelogenous leukemia, Hodgkin's disease, non-Hodgkin's lymphomas and multiple myeloma; childhood solid tumors such as brain tumors, glioblastoma, neuroblastoma, Rhabdomyosarcoma, retinoblastoma, Wilms tumor, bone tumors and soft-tissue sarcomas; and common adult solid tumors such as lung cancer, breast cancer, prostate cancer, urinary cancers, uterine cancers, oral cancers, pancreatic cancer, melanoma, skin cancers, stomach cancer, ovarian cancer, brain tumors, liver cancer, laryngeal cancer, thyroid cancer, esophageal cancer and testicular cancer.

The cancer in the present disclosure may be a cancer stem cell.

As used herein, the term "cancer stem cell" refers, in a broad sense, to cancer cells having self-renewal or differentiation ability, which is the unique ability of stem cells. The cancer stem cells are known to be present in tumors, and are believed to occur due to abnormal metastasis of the genetic information of normal stem cells. It is known that cancer stem cells are maintained and proliferated due to the presence of microenvironments (niches) for their survival, and that normal cells, immune-related cells or differentiated cancer cells, which are present around cancer stem cells, affect the maintenance of characteristics and proliferation of these cancer stem cells. In the normal tumor growth conditions of cancer stem cells (the "normal tumor growth conditions" refers to a state in which a nutrient (glucose) required for cell growth is sufficient and growth conditions for tumor microenvironments are abundant, and thus there is no cell stress), the cancer stem cells may proliferate at a slow rate, unlike common cancer cells, or may be maintained in a dormant state, and thus may have resistance to anticancer agents. For example, expression of transcription regulators may be controlled, unlike that in normal tumor cells, and thus the function of major metabolism regulatory substances therein may differ from that in common cancer cells. Thus, the term "cancer stem cells" generally refers to cells that acquire resistance to apoptosis in a nutrient-deficient state through this different metabolism regulatory ability and the regulation of cell signaling systems mechanistically linked thereto, and have invasive and/or metastatic potential. However, the cancer stem cells are not limited thereto and may include any cells that may differentiate into common cancer cells.

According to a further aspect of the present disclosure, the present disclosure provides a composition containing: the above-described monoclonal antibody or fragment thereof; a nucleic acid molecule encoding the same; a vector comprising the nucleic acid molecule; or an inhibitor that inhibits expression of the EPB41L5 gene.

According to a preferred embodiment of the present disclosure, the composition of the present disclosure may be used as a pharmaceutical composition for prevention or treatment of cancer or for inhibition of cancer metastasis.

In the composition of the present disclosure, contents related to the antibody or fragment thereof, nucleic acid molecule, cancer, cancer stem cell, etc. are the same as described above with respect to in the epitope, monoclonal antibody or fragment thereof, etc., and thus description thereof is omitted to avoid excessive complexity of the present specification.

The pharmaceutical composition of the present disclosure may comprise: (a) the antibody or fragment thereof; a nucleic acid molecule encoding the same; a vector comprising the nucleic acid molecule; or an inhibitor that inhibits expression of the EPB41L5 gene; and (b) a pharmaceutically acceptable carrier.

The greatest feature of the pharmaceutical composition of the present disclosure is that the pharmaceutical composition treats cancer or inhibits cancer metastasis by targeting the EPB41L5 gene or the protein encoded thereby and inhibiting the expression level of the EPB41L5 gene or the expression or activity of the EPB41L5 protein.

The inhibitor of the present disclosure may be one or more selected from the group consisting of siRNA (small interference RNA), shRNA (short hairpin RNA), miRNA (microRNA), ribozyme, DNAzyme, PNA (peptide nucleic acids), and antisense oligonucleotides. Preferably, the inhibitor is siRNA (small interference RNA) that binds specifically to the mRNA of the gene. As the inhibitor that inhibits expression of the EPB41L5 gene, the siRNA may be represented by the nucleotide sequence of SEQ ID NO: 4 or nucleotide sequence of SEQ ID NO: 5.

According to further another aspect of the present disclosure, the present disclosure provides a method for preventing or treating cancer, the method comprising a step of administering the pharmaceutical composition.

In the method for preventing or treating cancer according to the present disclosure, contents related to the pharmaceutical composition are the same as described above with respect to the pharmaceutical composition, and thus description thereof is omitted to avoid excessive complexity of the specification.

As used herein, the term "prevention" may include, without limitation, any action enabling the symptoms caused by cancer to be blocked or inhibited or delayed using the composition of the present disclosure.

As used herein, the term "treatment" may include, without limitation, any action enabling the symptoms caused by cancer to be alleviated or beneficially changed using the composition of the present disclosure. The pharmaceutically acceptable carrier that is contained in the vaccine composition and pharmaceutical composition of the present disclosure is a carrier that is commonly used for formulation, and examples thereof include, but are not limited to, lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil. The pharmaceutical composition of the present disclosure may further contain a lubricant, a wetting agent, a sweetening agent, a flavoring agent, an emulsifying agent, a suspending agent, a preservative, and the like, in addition to the above components. Suitable pharmaceutically acceptable carriers and formulations are described in detail in Remington's Pharmaceutical Sciences ($19^{th}$ ed., 1995).

The vaccine composition and pharmaceutical composition of the present disclosure may be administered orally or parenterally, preferably parenterally. For example, the composition may be administered by intravenous injection, local injection or intraperitoneal injection.

The appropriate dosage of each of the vaccine composition and the pharmaceutical composition of the present disclosure varies depending on factors such as the formulation method, the mode of administration, the patient's age, body weight, sex and pathological condition, diet, the duration of administration, the route of administration, excretion rate, and response sensitivity, and an ordinarily skilled physician can easily determine and prescribe an effective dosage for desired treatment or prevention. According to a preferred embodiment of the present disclosure, the daily dose of each of the vaccine composition and the pharmaceutical composition of the present disclosure is 0.0001 to 100 mg/kg.

The vaccine composition and pharmaceutical composition of the present disclosure may be formulated in unit dosage forms or in multi-dosage packages using a pharmaceutically acceptable carrier and/or excipient according to a method that may be easily carried out by those skilled in the art. At this time, the formulation may be a solution, suspension or emulsion in oil or aqueous medium, or an extract, powder, granule, tablet or capsule, and may further contain a dispersing agent or a stabilizer.

Each of the vaccine composition and pharmaceutical composition of the present disclosure may be used as a single therapy, but may also be used in combination with other conventional chemotherapy or radiotherapy. When this combination therapy is performed, cancer treatment may be more effectively achieved. Chemotherapeutic agents that may be used together with the composition of the present disclosure include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastine, and methotrexate. Radiotherapies that may be used together with the composition of the present disclosure include X-ray radiation and γ-ray radiation.

According to another aspect of the present disclosure, the present disclosure provides a method of providing information for diagnosis of a disease caused by overexpression of EPB41L5.

In the present disclosure, the method comprises steps of: (a) obtaining a sample isolated ex-vivo from a subject; (b) treating the sample with the monoclonal antibody or fragment thereof; and (c) determining whether the expression level of EPB41L5 contained in the sample from the subject is higher than the expression level of EPB41L5 contained in a normal sample.

In the method of providing information according to the present disclosure, contents related to the disease caused by overexpression of EPB41L5, cancer, cancer stem cells, monoclonal antibody, etc., are the same as described above, and thus description thereof is omitted to avoid excessive complexity of the specification.

According to still another aspect of the present disclosure, the present disclosure provides a method for quantifying the amount of EPB41L5 contained in a sample, the method comprising a step of treating the sample with the monoclonal antibody or fragment thereof.

Since the monoclonal antibody or fragment thereof according to the present disclosure binds specifically to EPB41L5, the use thereof makes it possible to accurately measure the amount of EPB41L5 contained in the sample.

In the method for quantifying the amount according to the present disclosure, contents related to the disease caused by overexpression of EPB41L5, cancer, cancer stem cells, monoclonal antibody, etc., are the same as described above, and thus description thereof is omitted to avoid excessive complexity of the specification.

According to yet another aspect of the present disclosure, the present disclosure provides a kit for quantifying the amount of EPB41L5, the kit comprising the monoclonal antibody or fragment thereof.

The kit for quantifying the amount according to the present disclosure may quantify the amount of EPB41L5 by analyzing the antigen against the antibody through an antigen-antibody binding reaction. The antigen-antibody binding reaction is preferably performed by one selected from the group consisting of conventional ELISA (enzyme-linked immunosorbent assay), RIA (radioimmnoassay), sandwich assay, Western blotting on polyacrylamide gel, immunoblot assay, and immunohistochemical staining, but is not limited thereto.

A support that is used for the antigen-antibody binding reaction of the present disclosure may be selected from the group consisting of a nitrocellulose membrane, a PVDF membrane, a well plate synthesized using polyvinyl resin or polystyrene resin, and slide glass, but is not limited thereto.

The secondary antibody is preferably labeled with a conventional coloring agent for a color development reaction. Specifically, it is possible to use any one labeling agent selected from the group consisting of fluoresceins such as HRP (horseradish peroxidase), alkaline phosphatase, colloidal gold, FITC (poly L-lysine-fluorescein isothiocyanate or RITC (rhodamine-B-isothiocyanate), and dyes. A substrate for inducing color development is preferably chosen depending on the labeling agent for color development reaction. Specifically, the substrate is preferably any one selected from the group consisting of TMB (3,3',5,5'-tetramethylbenzidine), ABTS [2,2'-azino-bis(3-ethylbenzothiazoline)-6-sulfonic acid)] and OPD (o-phenylenediamine), but is not limited.

Advantageous Effects

The features and advantages of the present disclosure are summarized as follows:

(1) The present disclosure provides a monoclonal antibody and a fragment thereof that recognizes EPB41L5 as an antigen and binds specifically thereto.

(2) The present disclosure may be used to identify an antibody that binds specifically to an epitope of EPB41L5, and an antibody identified through this method functions to inhibit EPB41L5 signaling and, and this function enables the antibody to be effectively used as a vaccine or therapeutic agent against cancer in which EPB41L5 is involved, particularly gastric cancer.

BRIEF DESCRIPTION OF DRAWINGS

FIG. 1A shows the results of performing oligonucleotide microarray analysis in gastric cancer patients without lymph node metastasis. The gastric cancer patients were classified into two groups according to their gene expression patterns (based on the median expression level of EPB41L5).

FIG. 2A shows the results of analyzing various gastric cancer cells by Western blotting.

FIG. 2B is a graph showing the results of analyzing the expression level of EPB41L5 gene by performing real-time qPCR on gastric cancer cells treated with TGF-R1 (10 ng/ml) for 24 hours and on gastric cancer cells not treated cells with TGF-β1. Here, control indicates EPB41L5 mRNA expression in gastric cancer cells not treated with TGF-β1, and TGF-β1 indicates EPB41L5 mRNA expression in gastric cancer cells treated with TGF-β1.

FIG. 2C shows the results of analyzing the expression levels of EMT-related genes (EPB41L5, p-Smad2, Smad2, p-Smad3, Smad3, PAI-1, and P-actin) by performing Western blot analysis on gastric cancer cells treated with TGF-β1 (10 ng/ml) for 24 hours and on gastric cancer cells not treated cells with TGF-β1.

FIG. 2D shows the results of analyzing the expression levels of endogenous EPB41L5 and E-cadherin in NCI-N87 cells and KATOIII cells treated with TGF-β1 (10 ng/ml) for 24 hours and in NCI-N87 cells and KATOIII cells (control) not treated with TGF-β1. Here, scale bars represent 20 μm.

FIG. 2E depicts images showing the cell morphologies of KATOIII and SNU719 cells treated or not treated with TGF-β1. The cell morphology according to the presence or absence of TGF-β1 was observed through FIG. 2E. White arrows indicate cells transformed to mesenchymal cells. Exposed KATOIII and SNU719 cells. Scale bars represent 20 m.

FIG. 3A shows the results of performing Western blot analysis after MKN45 cells and NCI-N87 cells deficient in Smad4 expression were treated or not treated with TGF-β1.

FIG. 3B shows the results of immunofluorescent staining analysis performed to analyze the expression levels of endogenous EPB41L5 and E-cadherin in NCI-N87 cells treated or not treated with TGF-β1. Here, scale bars represent 20 μm.

FIG. 3C is a graph showing the results of analyzing the mRNA (fold induction) of each of Smad4, EPB41L5, Slug and PAI-1 in KATOIII cells treated or not treated with TGF-β1 or siSMAD4 #1 or #2. Experimental results are expressed as mean±s.e.m, and scale bars represent 20 m. *P<0.05, P<0.01, *P<0.001.

FIG. 3D shows the results of analyzing the expression levels of EMT-related genes (EPB41L5, p-Smad4, αPAI-1, αSlug, and α-tubulin) by performing Western blot analysis on KATOIII cells treated with TGF-β1 (10 ng/ml) or siSmad4 #1 or #2 and on untreated KATOIII cells.

FIG. 5E shows the results of performing in vitro migration and invasion analysis on NC (negative control) siRNA-transfected KATOIII cells and EPB41L5 siRNA #1- or EPB41L5 siRNA #2-transfected KATOIII cells depending on the presence or absence of TGF-β1. Experimental results are expressed as mean±s.e.m. *P<0.05, P<0.01, *P<0.001.

FIGS. 6A-6H relate to the specificity of an anti-EPB41L5 monoclonal antibody. FIG. 6A shows the results of performing Western blot analysis on MKN28 cells transfected with a Flag-EPB41L5 construct, and FIG. 6B shows the results of performing Western blot analysis on MKN28 cells transfected with EPB41L5 siRNA (#1 or #2).

FIG. 6C shows the results of performing immunofluorescent staining of EPB41L5 siRNA-transfected MKN28 cells (EPB41L5 siRNA).

FIG. 6D is a schematic view showing the structure of an EPB41L5 domain.

FIG. 6E shows the results of performing Western blot analysis on 293T cells transfected with each of the FL (full length) of EPB41L5, the FERM of EPB41L5 and the C-terminus of EPB41L5.

FIG. 6F shows the results of analyzing Western blot analysis on total lysates of 293T cells transfected with plasmids (1-633, 1-628, 1-623, 1-618, and 1-613) in which five amino acid residues at the C-terminus of EPB41L5 are continuously deleted.

FIG. 6G shows the results of analyzing Western blot analysis on total lysates of 293T cells transfected with plasmids consisting of FL (full length) of EPB41L5 and A619-624 of EPB41L5, respectively.

FIG. 6H shows the results of performing immunofluorescent staining of MKN28 cells co-transfected with EPB41L5 siRNA and any one selected from among FL (full length) of EPB41L5, FERM of EPB41L5, the C-terminus of EPB41L5, and A619-624 of EPB41L5. At this time, the immunofluorescent staining was performed using anti-EPB41L5 mAb and anti-Flag antibodies. Here, scale bars represent 20 μm.

FIG. 9A shows the results of performing in vitro migration and invasion analysis on EPB41L5-overexpressing KATOIII cells and control cells (vehicle). At this time, 1% FBS was used as a chemoattractant.

FIG. 9B shows quantification of the results of performing in vitro migration and invasion analysis on EPB41L5-overexpressing KATOIII cells and control cells (vehicle). 15 random cells were selected from each group and quantified by cell counting using Fusion Capt advanced software. Experimental data are expressed as mean±s.e.m.

FIG. 9C shows the results obtained by injecting EPB41L5-overexpressing KATOIII cells (GFP-labeled) (EPB41L5(GFP)) into nude mice through the tail vein (10 mice per group) and analyzing lung metastasis of the cells using an IVIS optical imaging system. FIG. 9D shows the results of quantifying the intensity, measured from the images of FIG. 9C, using an ROI tool. Experimental data are expressed as average radiant efficiency±s.e.m. *P<0.05 and **P<0.01.

BEST MODE

Figure 1A:
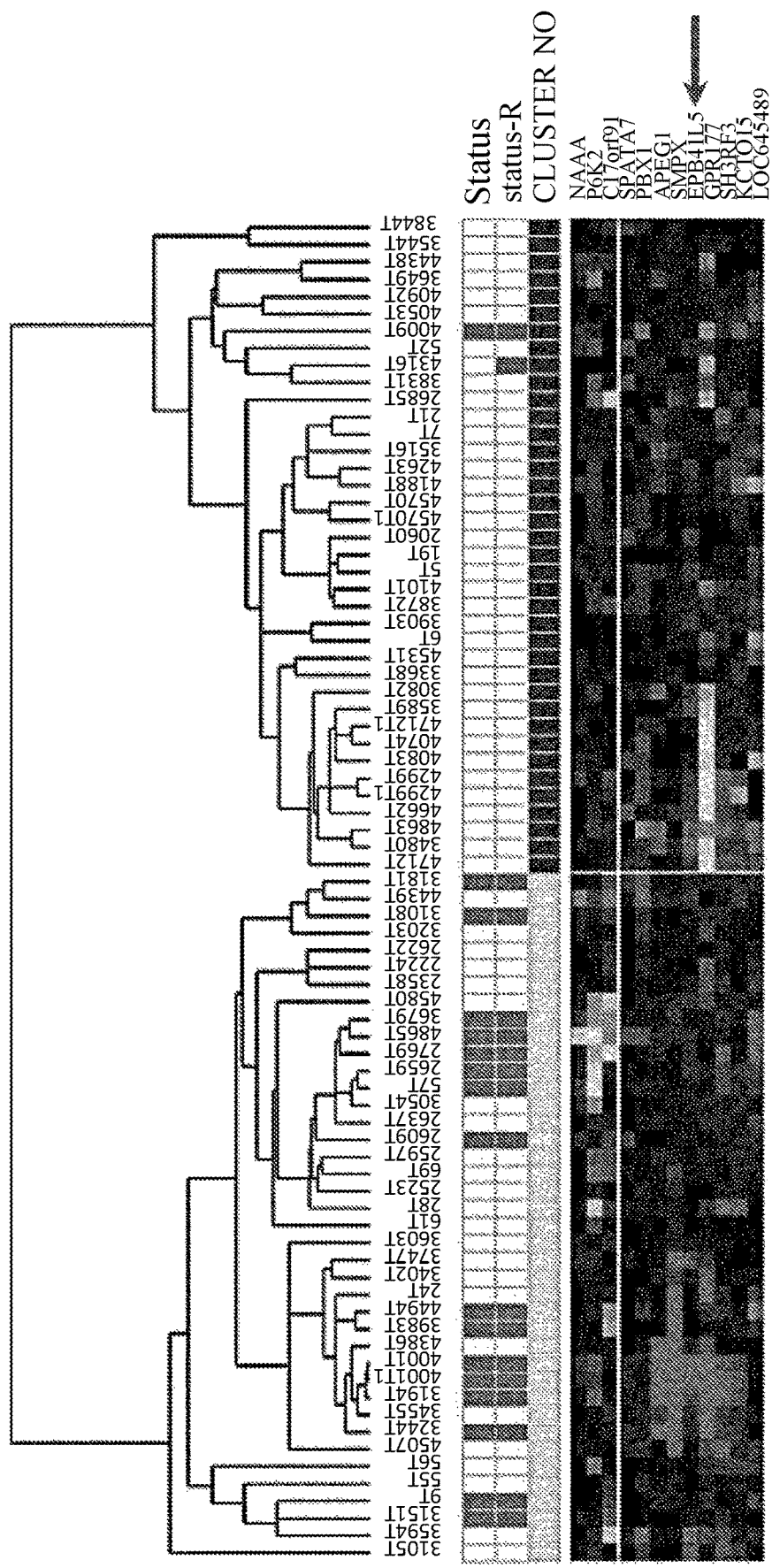
FIG. 1A shows the results of performing microarray analysis in gastric cancer patient specimens, which indicate that, when the expression level of EPB41L5 is high, the prognosis of gastric cancer patients is poor.

According to one embodiment of the present disclosure, there are provided: an epitope comprising the $619^{th}$ to $624^{t}$ amino acid residues of an EPB41L5 protein represented by the amino acid sequence of SEQ ID NO: 1; and a vaccine composition for preventing or treating cancer containing the same.

According to another embodiment of the present disclosure, there is provided a monoclonal antibody or fragment thereof comprising: a heavy-chain variable region comprising a heavy-chain CDR1 represented by SEQ ID NO: 6, a heavy-chain CDR2 represented by SEQ ID NO: 7, and a heavy-chain CDR3 represented by SEQ ID NO: 8; and a light-chain variable region comprising a light-chain CDR1 represented by SEQ ID NO: 9, a light-chain CDR2 represented by SEQ ID NO: 10, and a light-chain CDR3 represented by SEQ ID NO: 11.

According to still another embodiment of the present disclosure, there is provided a composition for preventing or treating cancer containing the monoclonal antibody or fragment thereof as an active ingredient.

MODE FOR INVENTION

Hereinafter, the present disclosure will be described in more detail with reference to examples. It will be obvious to those skilled in the art that these examples serve to merely describe the present disclosure in more detail, and the scope of the present disclosure according to the subject matter of the present disclosure is not limited by these examples.

Experimental Methods

1. Patient Specimens

Gastric cancer patient specimens for oligonucleotide microarray and survival rate analysis were obtained from the Clinical Test Center, Severance Hospital (IRB No: 4-2016-0013).

2. Cell Culture and Reagents

Human gastric cancer cell lines AGS, NCI-N87, $KATO^2$, SK-GT-4, MKN1, MKN28, MKN45, SNU1, SNU5, SNU16, SNU216, SNU484, SNU638, SNU668 and SNU719 were obtained from professor Cheong Jae-Ho lab at Yonsei University (Seoul, Korea).

All the gastric cancer cells were cultured in RPMI-1640 medium supplemented with 10% FBS and 1% antibiotic/antimycotic solution (Corning, Manassas, VA, USA)) at 37° C. under 5% $CO_2$. 293FT cells were cultured in DMEM. TGF-β1 was purchased from Prospec (East Brunswick, NJ, USA), and LY2157299 was purchased from Selleckchem (Houston, TX, USA).

3. Plasmids

EPB41L5-relevant DNA constructs encoding full-length, FERM domain, C-terminus, A619-624 and C-terminal 5 amino acids, which were sequentially removed, were generated by PCR and cloned into the pSG5-KF2M1-Flag (Sigma-Aldrich, St. Louis, MO, USA). All plasmid constructs were verified by DNA sequencing.

4. siRNA Transfection

Cells were transfected with siRNAs using Lipofectamine RNAiMAX (Thermo Fisher Scientific, Rockford, IL, USA) according to the manufacturer's procedure. siRNAs used were synthesised by Genolution (Seoul, South Korea) and had the following siRNA sequences: EPB41L5-1 (EPB41L5 siRNA #1; siEPB41L5 #1) (SEQ ID NO:4; 5'-GCAAUUGGCAGCUUAUAAUUU-3'), EPB41L5-2 (EPB41L5 siRNA #2; siEPB41L5 #2) (SEQ ID NO:5; 5'-UUCAGAUUC GUGCCUAUUCAGUU-3'), Smad4-1 (SEQ ID NO:14; 5'-GCUACUUACCAUCAU AACAUU-3'), and Smad4-2 (SEQ ID NO: 15; 5'-GUUCCAUUGC-UUACUUUUUUUUU-3').

5. Monoclonal Antibody) Anti-EPB41L5 mAb

Monoclonal antibody was produced by immunizing mice with the $386^{th}$ to $637^{th}$ amino acid residues (SEQ ID NO: 3) of human EPB41L5 antigen, and this production was carried out by ATgen (Seongnam, Korea).

1) Immunization of Mice and Production of Hybridoma Cells

Monoclonal antibody was produced using the $386^{th}$ to $637^{th}$ amino acid residues (SEQ ID NO: 3) of human EPB41L5 antigen. For efficient production of the antibody, SEQ ID NO: 3 was selected as a target peptide for antibody production.

The target peptide for antibody production (SEQ ID NO: 3) was injected into mice, and cells producing the antibody against the antigen were generated. The antibody-producing cells (B lymphocytes) obtained from the spleen of the mice were fused with myeloma cells to obtain hybridoma cells. The hybridoma cells were cultured in HAT medium in which only hybridoma cells can survive, and then the activity of the antibody was analyzed by ELISA assay.

2) Selection and Identification

Among the hybridoma cells, monoclonal hybridoma cells that specifically recognize EPB41L5 were selected, and the selected monoclonal hybridoma cells were injected into the abdominal cavity of mice, and then monoclonal antibody was recovered from ascites. The monoclonal antibody of the present disclosure, recovered from ascites, was purified using protein A and protein G columns.

Thereafter, a monoclonal antibody (EPB41L5 mAb) that specifically recognizes EPB41L5 was selected and identified by Western blot analysis and immunofluorescent staining using the EPB41L5 construct and siRNA.

6. Generation of EPB41L5-Overexpressing Stable Cell Lines

EPB41L5 DNA was cloned into the pCDH-CMV-MCS-EF1-puro vector (Addgene, Cambridge, MA, USA). To generate lentiviral particles, packaging plasmids pRSV-Rev and pMD2.G were transfected with pCDH-EPB41L5 or pLECE3-GFP in 293FT cells. After 48 hours of incubation, the supernatants were collected and filtered with a 0.45-μm pore filter. The KATO$^2$ cells were infected with lentiviral particles and then selected with 1 μg/ml puromycin (Sigma-Aldrich). The selected stable EPB41L5-overexpressing cells were sorted with GFP by an Aria II flow cytometer (BD Biosciences, Sparks, MD, USA).

7. Western Blot Analysis

Cells were lysed in lysis buffer (20 mmol/L Tris-Cl, 150 mmol/L NaCl, 1% Triton X-100, 1.5% $MgCl_2$, 1 mMEDTA, 1 mM $Na_2VO_4$, 1 mM phenylmethylsulfonyl fluoride (PMSF), and protease inhibitor cocktail, pH 7.5). The lysates were vortexed briefly and centrifuged at 13,000 rpm for 20 minutes at 4° C. The supernatants were collected and transferred into fresh tubes. Protein concentrations were measured at 660 nm using protein assay reagent (Thermo Fisher Scientific). Equal concentrations of protein samples were prepared, and each sample was electrophoresed on SDS-polyacrylamide gel and then transferred to nitrocellulose membranes (Whatman, Dassel, Germany). The membranes were blocked in Tris-buffer (pH 7.4) containing 0.1% (v/v) Tween 20 (Sigma-Aldrich) and 5% (w/v) nonfat Difco™ skim milk (BD Biosciences) and probed with primary antibodies. The following antibodies were used: polyclonal EPB41L5 (Thermo Fisher Scientific); EPB41L5 (ATGen, Seongnam, Korea); Flag-tag, β-actin (Sigma-Aldrich); α-tubulin (Abcam, Cambridge, GB), TORI, TORII, Smad2, Smad3, Smad4, p-Smad2, p-Smad3, Slug, ZEB1 (Cell signaling, Danvers, MA, USA); and PAI-1 (Santa Cruz, Dallas, TX, USA). The signals were developed by substrate (Thermo Fisher Scientific) according to the manufacturer's protocol.

8. RNA Isolation and Real-Time qPCR

Total RNA was extracted using TRIzol reagent (Takara Bio, Otsu, Shiga, Japan), and cDNA was synthesised using PrimeScript Reverse Transcriptase (Takara Bio, Otsu, Shiga, Japan) and oligo(dT) according to the manufacturer's protocol. quantitative PCR (qPCR) was performed using SYBR Green Master (Roche, Basel, Switzerland) and ABI Prism 7700 sequence detection systems (Applied Biosystems, Carlsbad, CA, USA). The following primers were used to detect transcripts: α-tubulin (SEQ ID NO:16; 5'-TTCTC-CATTTACCCGGCACC-3') and (SEQ ID NO:17; 5'-GTTAGTGTAGGTTGGGCGCT-3'); EPB41L5 (SEQ ID NO:18; 5'-GAAA GAAGGCCCAGCAAACG-3') and (SEQ ID NO:19; 5'-AGATCTCATCCCCCAAGCCT-3'); PAI-1 (SEQ ID NO:20; 5'-CCCCACTTCTTCAGGCTGTT-3') and (SEQ ID NO:21; 5'-GCCGTTGAA GTAGAGGGCAT-3'); Slug (SEQ ID NO:22; 5'-TCATCTTTGGGGCGAGT-GAG-3') and (SEQ ID NO:23; 5'-TGCAGCTGCT-TATGTTTGGC-3'); ZEB1 (SEQ ID NO:24; 5'-TATGAATGCCCAAACTGCAA-3') and (SEQ ID NO:25; 5'-TGGTGATGCTGAAAGAGACG-3'); Smad4 (SEQ ID NO:26; 5'-TGCATGACTTTGAGGGACAG-3') and (SEQ ID NO:27; 5'-GTGGAAGCCACAGGAATGTT-3'). The quantity of cDNA was normalized with u-tubulin. All experiments were performed in triplicate, and relative expression levels and standard deviations were calculated by the comparative method.

9. Immunofluorescence Analysis

Cells were cultured on chamber slides (SPL Life Sciences, Pocheon-shi, Korea) and fixed in 4% paraformaldehyde for 30 minutes at room temperature. After washing with PBS, the fixed cells were incubated for 1 hour with 3% BSA to block nonspecific antibodies. Anti-EPB41L5, anti-E-cadherin and anti-Flag-tag were incubated at 4° C. overnight and then stained with Alexa Fluor 488- or Alexa Fluor 549-conjugated goat anti-rabbit or anti-mouse secondary antibody (Thermo Fisher Scientific). The nuclei were stained with Hoechst 33258. The samples were imaged with an LSM710 confocal microscope (Carl Zeiss, Oberkochen, Germany).

10. In Vitro Migration and Invasion Assay

Cell migration was measured by Transwell with 8.0-μm pore polycarbonate membrane insert (Corning, Manassas, VA, USA). For invasion assay, inserts of the Transwell were coated with Matrigel (BD Biosciences). $1 \times 10^5$ cells per well were added to the upper chamber, and the lower chamber was filled with 600 μL of serum-free medium with or without TGFβ1, LY2157299 (TGFβ inhibitor), or anti-EPB41L5 monoclonal antibody (mAb) as a chemoattractant. After 24 hours of incubation, nonmigrating or noninvading cells were carefully removed from the upper chamber by a cotton swab. Migrating or invading cells were stained with 0.2% crystal violet (Sigma-Aldrich) in 20% methanol and counted at ×200 magnification under a microscope. The migration and invasion assays were performed in triplicate.

11. In Vivo Metastasis Assay 5-week-old athymic BALB/c nu/nu mice were obtained from Orient (Seoul, Korea). Control vector or pCDH-EPB41L5- and pLECE3-GFP-overexpressing KATO$^2$ cells ($2 \times 10^7$ cells in 200 μL PBS solution) were injected into the lateral tail vein. Anti-EPB41L5 monoclonal antibody was administered at 5 mg/kg every day for 2 weeks. The fluorescence images were taken and analyzed with an IVIS imaging system (Caliper Life Sciences, Hopkinton, MA, USA).

12. Statistical Analysis

The overall survival rate in the data obtained from gastric cancer patient specimens was analyzed using the Kaplan-Meier Plotter (http://kmplot.com/analysis). Used Affymetrix ID was220977_x_at, and the log-rank test was used for Kaplan-Meier survival plots. Statistical analysis was performed using the Student t test to compare two groups of independent experiments (two sided). The data were expressed as mean standard deviation (SD). P values <0.05 were considered statistically significant.

EXAMPLES

<Example 1>. Analysis of Expression Level of EPB41L5 Gene in Gastric Cancer Patient Specimens To identify potential target molecules in GC, oligonucleotide microarray analysis was performed in 78 gastric cancer patients without lymph node metastasis. The patients were divided into two groups (first and second groups) based on the median expression level of EPB41L5 gene. With respect to the median expression level of EPB41L5 gene, the first group is positioned on the left side and the second group is positioned on the right side.

Figure 1B:
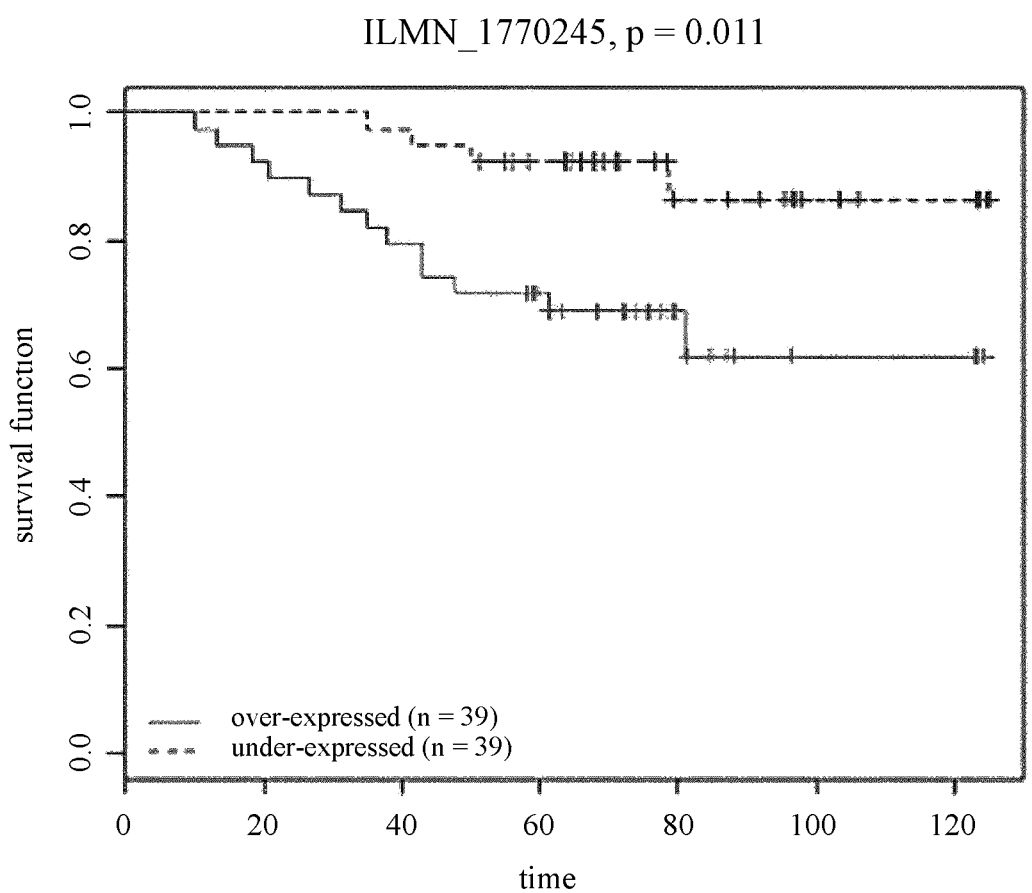
FIG. 1B is a graph showing the results of analyzing the 10-year survival rates of two groups of gastric cancer patients.

It was confirmed that the first group with highly expressed APEG1, SMPX, GPR177 and EPB41L5 genes had a higher rate of recurrence or death than the second group in which the expression levels of the genes were not high (FIG. 1A). Among the APEG1, SMPX, GPR177 and EPB41L5 genes, EPB41L5 was selected as a target protein for antibody-based cancer therapy. As a result of analyzing the future 10-year survival rate of the two groups divided based on the median expression level of the EPB41L5 gene (FIG. 1B), it can be seen that the survival rate of the patients with high expression levels of the EPB41L5 gene is lower than that of the patients with low expression levels of the EPB41L5 gene.

Figure 1C:
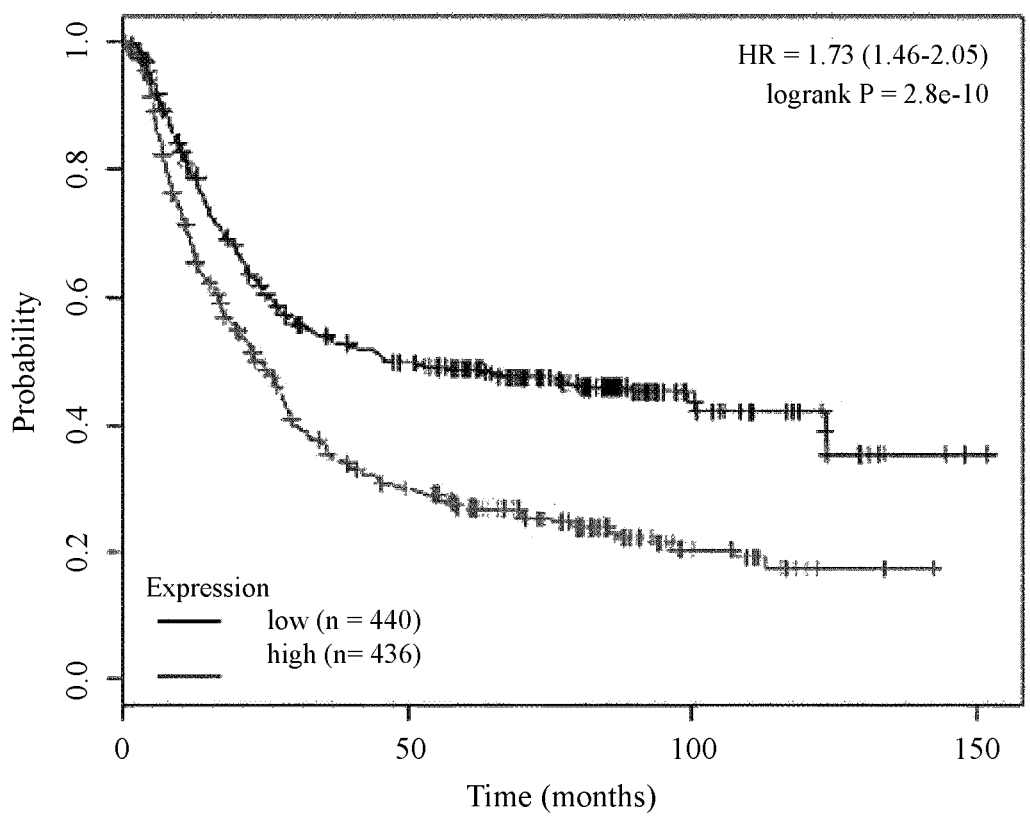
FIG. 1C shows the results of performing Kaplan Meier plot analysis on two groups of gastric cancer patients.

In addition, as a result of performing Kaplan Meier plot analysis on the two groups of cancer patients (876 gastric cancer patients), it was confirmed that, in the Kaplan Meier plotter using a database such as GEO, EGA or TCGA, gastric cancer patients with high levels of EPB41L5 expression had a lower survival rate (HR 1.73, P 2.8E-10) (FIG. 1C). These clinical outcomes show that high levels of EPB41L5 expression are related to poor prognosis in gastric cancer patients. In other words, gastric cancer patients with high levels of EPB41L5 gene expression had a lower survival rate.

Figure 2A:
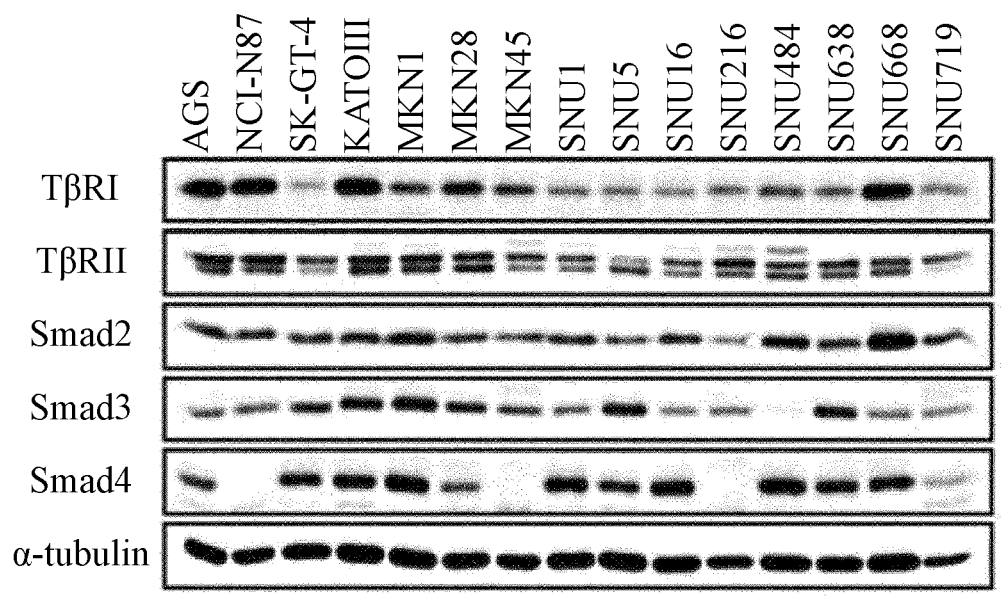
FIGS. 2A-2E show the data of various experiments performed to analyze whether EPB41L5 and mesenchymal gene expression has relevance with TGFβ signaling.

<Example 2>. Analysis of Expression Patterns of TGF-β1 and EPB41L5 Proteins in Gastric Cancer Cells The present inventors examined which gastric cancer cells were responsive to TGFβ signaling. The protein levels of proteins relevant to TGFβ signaling cascades were analyzed by performing Western blot analysis in several gastric cancer cell lines (FIG. 2A). As a result, it was confirmed that Smad3 or Smad4 was not detected in NCI-N87, MKN45, SNU216 and SNU484 cells.

Figure 2B:
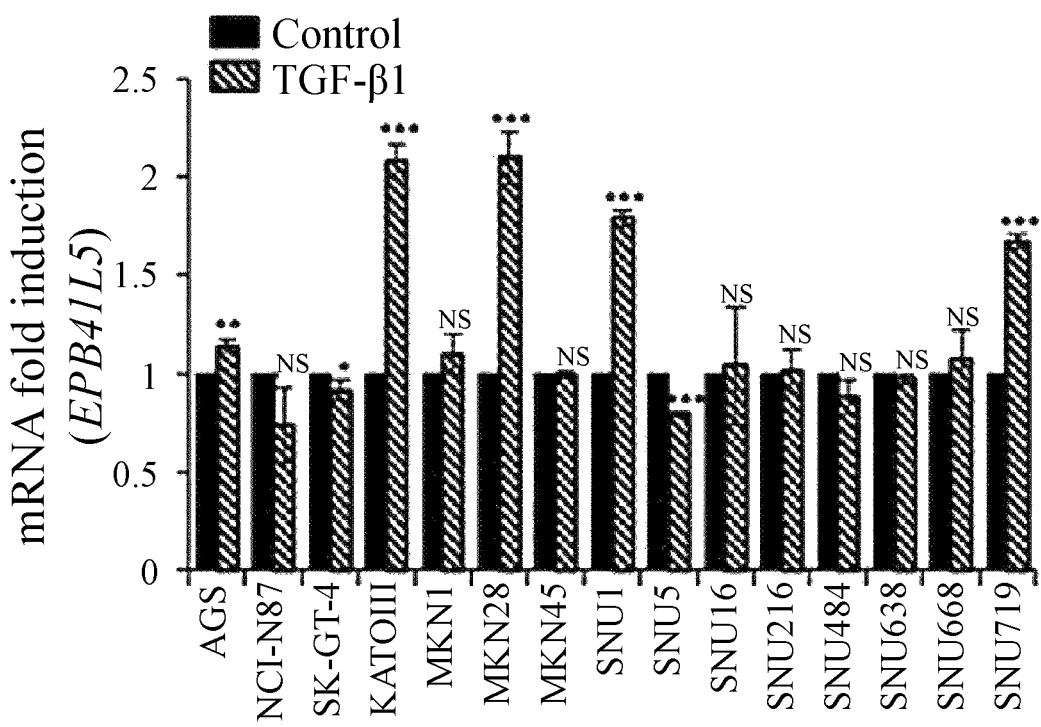
Figure 2C:
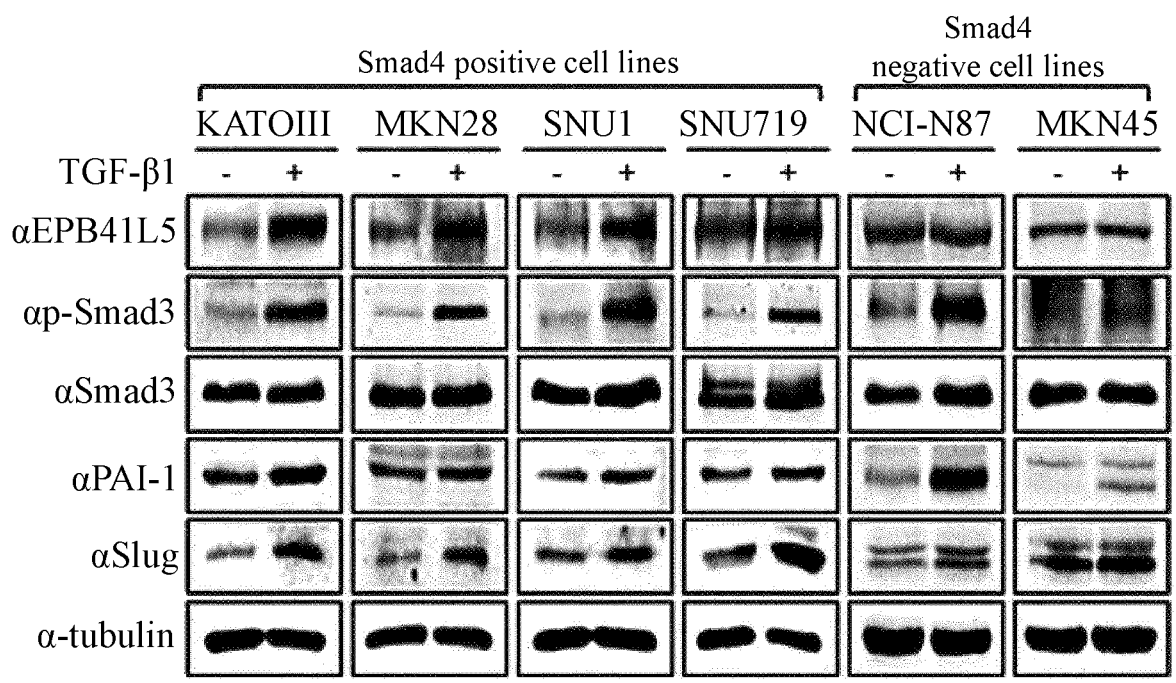

Next, gastric cancer cells were treated with TGF-β1 to examine whether EPB41L5 gene expression is regulated by TGFβ signaling. As a result, it was confirmed that the expression level of the EPB41L5 gene was significantly increased by TGF-β1 treatment in KATOIII, MKN28, SNU1 and SNU719 cells, but not in Smad3/Smad4-defective GC cells (FIG. 2B). In addition, expression of mesenchymal genes such as PAI-1, Slug and phosphorylated Smad2 and Smad3 was significantly increased by TGF-31 treatment (FIG. 2C).

Figure 2D:
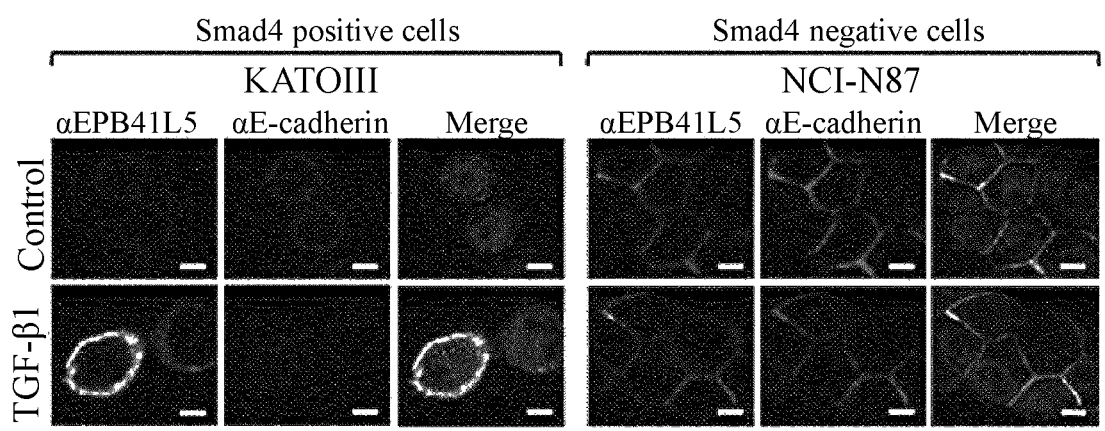
Figure 2E:
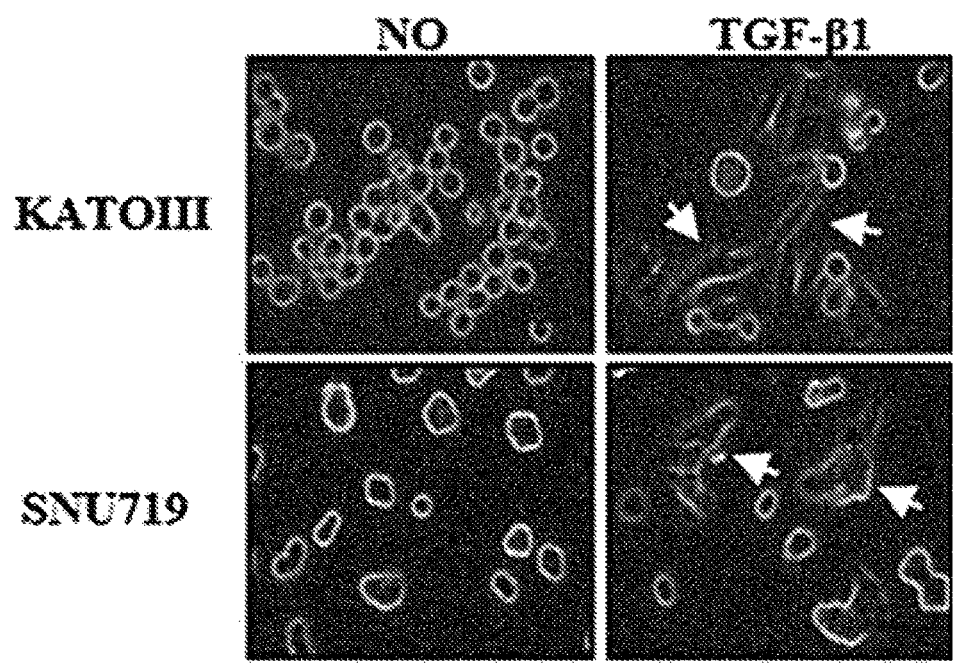

According to the results of immunofluorescence staining analysis (FIG. 2D), it was confirmed that expression of the epithelial marker E-cadherin in the transmembrane decreased and the expression level of EPB41L5 protein was increased by TGF-β1 in the cell membrane of KATOIII. In addition, the morphologic characteristics of gastric cancer cells KATOIII and SNU719 were changed to mesenchymal characteristics by TGFβ1 treatment (FIGS. 2E and 2F).

These results suggest that TGFβ signaling regulates the expression levels of the EPB41L5 gene and the protein encoded thereby and epithelial-mesenchymal transition in cancer cells, for example, gastric cancer cells.

<Example 3>. Regulation of Expression Level of EPB41L5 Protein by Smad-Dependent TGFβ Signaling To examine whether the TGFβ1-induced increase in the expression level of the EPB41L5 protein is Smad-dependent, Western blot analysis and immunofluorescent staining were performed in Smad4-deficient MKN45 (Smad4-knocked down MKN45) and NCI-N87 cells (gastric cancer).

Figure 3A:
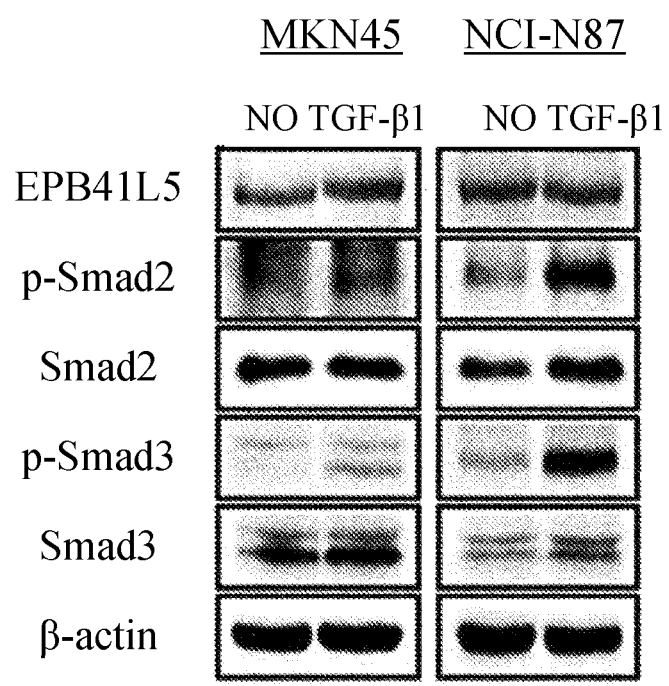
FIGS. 3A-3D show the results of an experiment performed to confirm that Smad-depending TGFβ signaling may regulate EPB41L5 expression.
Figure 3B:
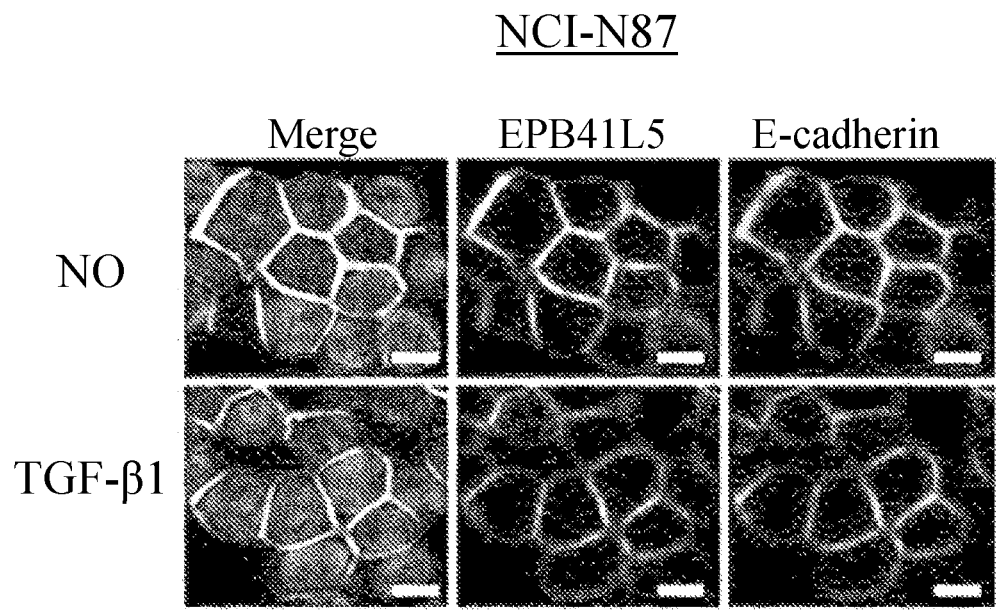
Figure 3C:
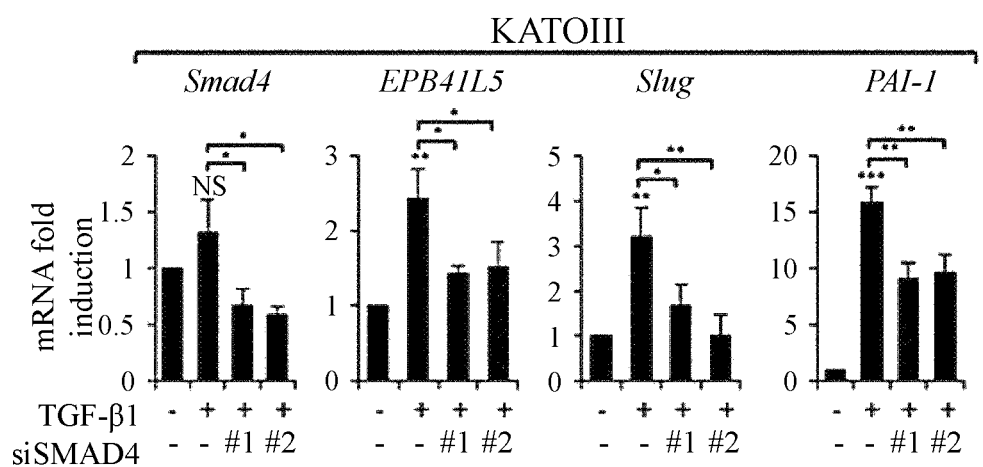
Figure 3D:
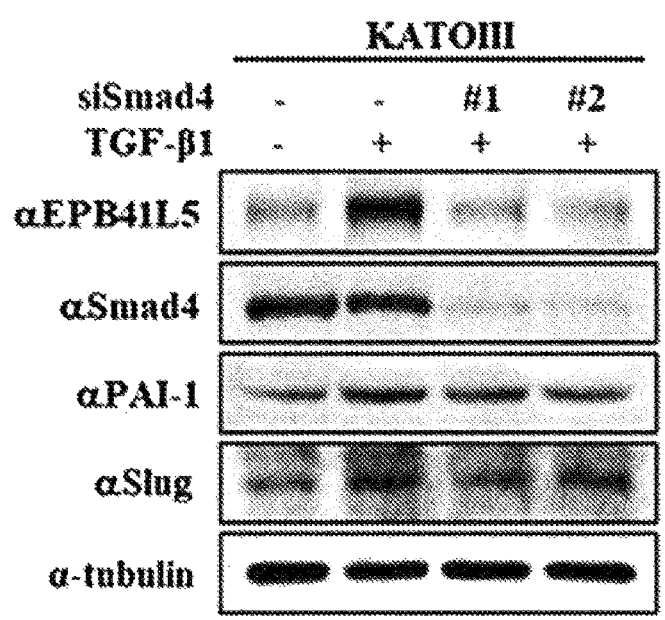

It was confirmed that the levels of these genes and the EPB41L5 proteins in each type of cells treated with TGF-β1 did not change (FIGS. 3A and 3B). In addition, it was confirmed that EPB41L5, PAI-1 and Slug in each type of cells treated with TGF-β1 were upregulated, and expression of EPB41L5, PAI-1 and Slug in MKN28 cells, in which Smad4 was knocked down using siRNA, was inhibited (FIGS. 3C and 3D).

Taking these results together, it can be seen that TGFβ signaling is Smad-dependent, indicating that TGFβ signaling is involved in the regulation of EPB41L5 expression in gastric cancer cells.

<Example 4>. Analysis of Relevance of TGF-p1 with EPB41L5 Protein

In the present disclosure, changes in the expression level of the EPB41L5 protein by treatment with the potent TGFβ receptor I inhibitor LY2157299 (Galunisertib) were analyzed.

Figure 4:
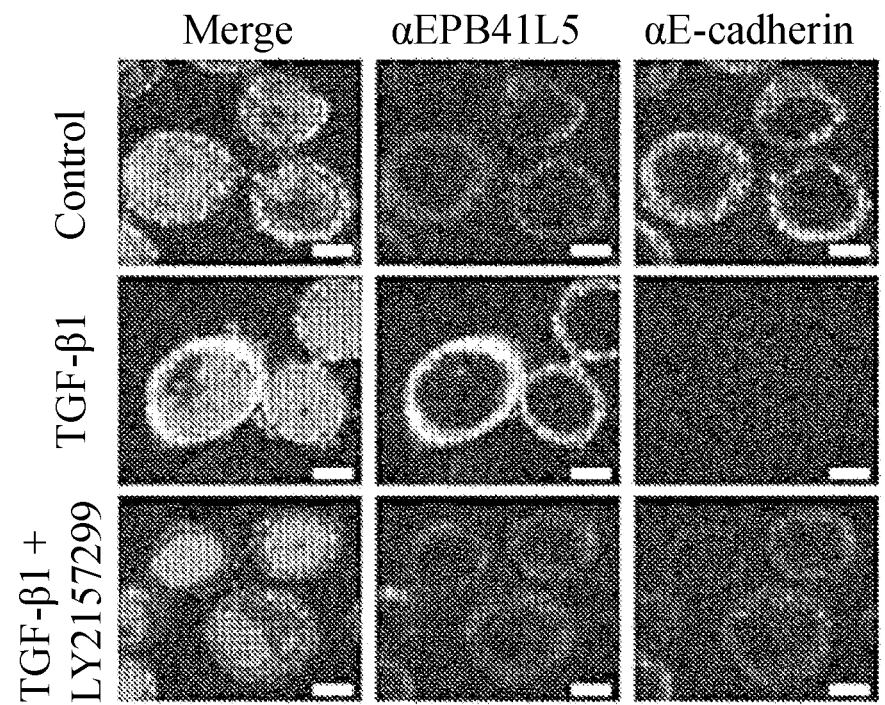
FIG. 4 shows the results of immunofluorescent staining performed to analyze expression of endogenous EPB41L5 and E-cadherin in untreated KATOIII cells, KATOIII cells treated with only TGF-β1, and KATOIII cells treated with TGF-β1 and then with a TGFβ inhibitor (LY2157299). Here, scale bars represent 20 μm.

FIG. 4 shows the results of immunofluorescent staining performed to analyze expression of endogenous EPB41L5 and E-cadherin in untreated KATOIII cells, KATOIII cells treated with only TGF-β1, and KATOIII cells treated with TGF-β1 and then with a TGFβ inhibitor (LY2157299). Here, scale bars represent 20 μm.

As shown in FIG. 4, as a result of performing immunofluorescent staining of KATOIII cells treated with only TGF-β1 and KATOIII cells treated sequentially with TGF-β1 and LY2157299, it was confirmed that the expression level of the EPB41L5 protein was increased by TGF-β1, but was inhibited by LY2157299.

<Example 5>. Analysis of Effect of EPB41L5 on Migration of Gastric Cancer Cells

Figure 5A:
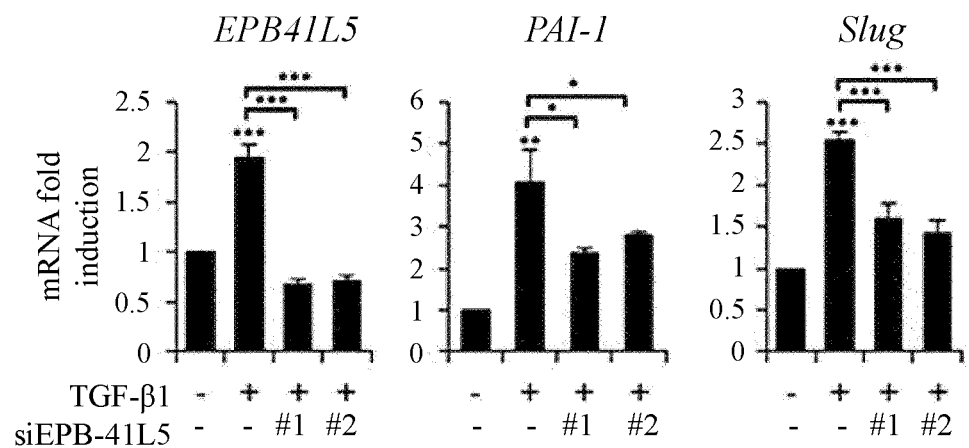
FIG. 5A shows the results of performing real-time qPCR on NC siRNA-transfected KATOIII cells, and EPB41L5 siRNA #1- or EPB41L5 siRNA #2-transfected KATOIII cells depending on the presence or absence of TGF-β1 in order to confirm that the migration of gastric cancer cells caused by EPB41L5 is regulated by treatment with TGF-β1.
Figure 5B:
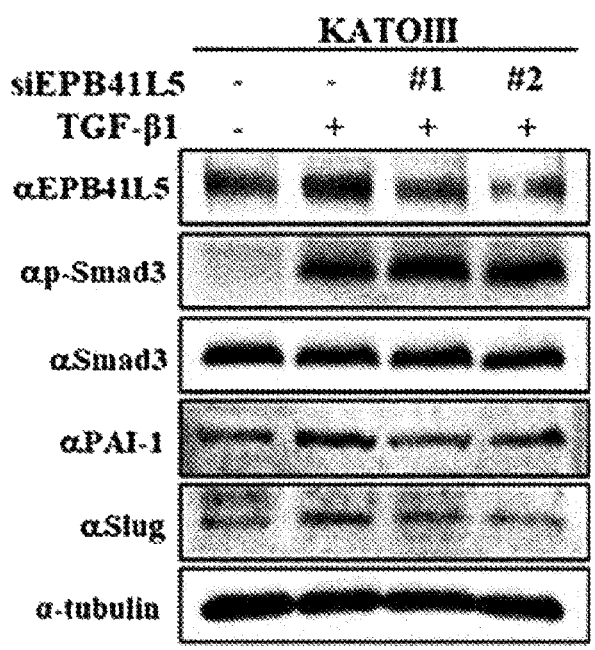
FIG. 5B shows the results of performing Western blot analysis on NC siRNA-transfected KATOIII cells, and EPB41L5 siRNA #1- or EPB41L5 siRNA #2-transfected KATOIII cells depending on the presence or absence of TGF-β1.

Whether EPB41L5 affects the migration of gastric cancer cells in response to TGFβ signaling was examined. To this end, KATOIII cells or SNU719 cells were transfected with EPB41L5 siRNA. Specifically, two types of siRNAs (EPB41L5 siRNA #1 (SEQ ID NO 4: 5'-GCAAUUGGCAGCUUAUAAUUU-3'), and EPB41L5 siRNA #2 (SEQ ID NO 5: 5'-UUCAGAUUC GUGCC-UAUUCAGUU-3')) were used for knockdown of EPB41L5. It was confirmed that the gene and protein levels of EPB41L5 and PAI-1 in the KATOIII cells transfected with EPB41L5 siRNA #1 or EPB41L5 siRNA #2 significantly decreased compared to those in the KATOIII cells transfected with NC siRNA (FIGS. 5A and 5B). However, in the KATOIII cells transfected with EPB41L5 siRNA #1 or EPB41L5 siRNA #2, changes in phosphorylated Smad3 (up-Smad3) and Smad3 (αSmad3) were not observed (FIG. 5B).

Figure 5C:
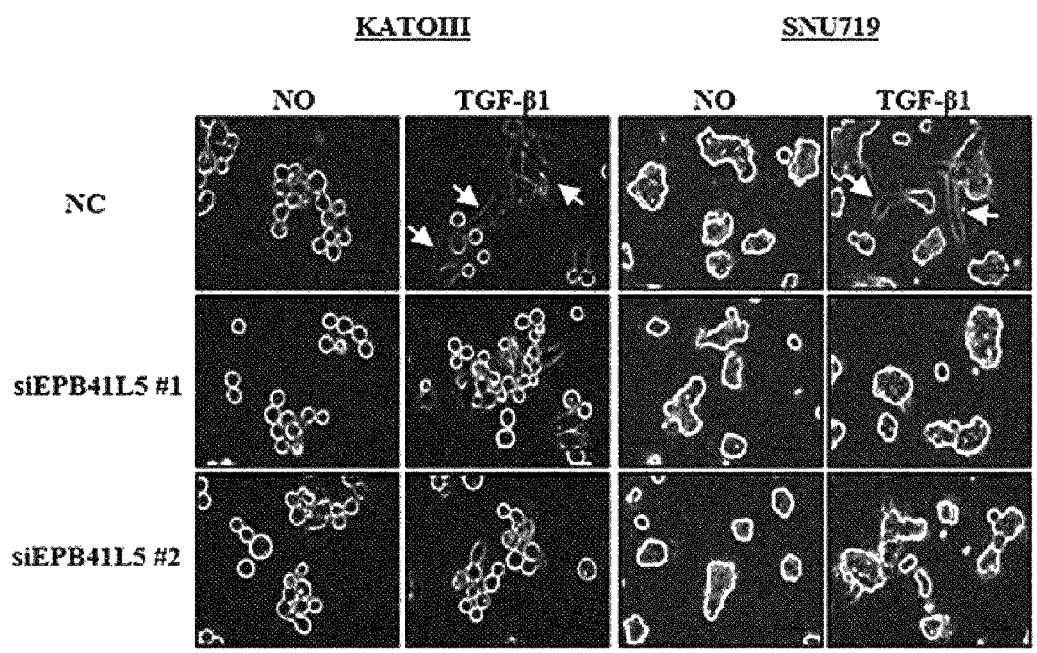
FIG. 5C shows the results of measuring morphological changes of NC siRNA-transfected KATOIII cells, EPB41L5 siRNA #1- or EPB41L5 siRNA #2-transfected KATOIII cells and SNU719 cells depending on the presence or absence of TGF-β1. White arrows indicate cells transformed to mesenchymal cells, and scale bars represent 20 μm.
Figure 5D:
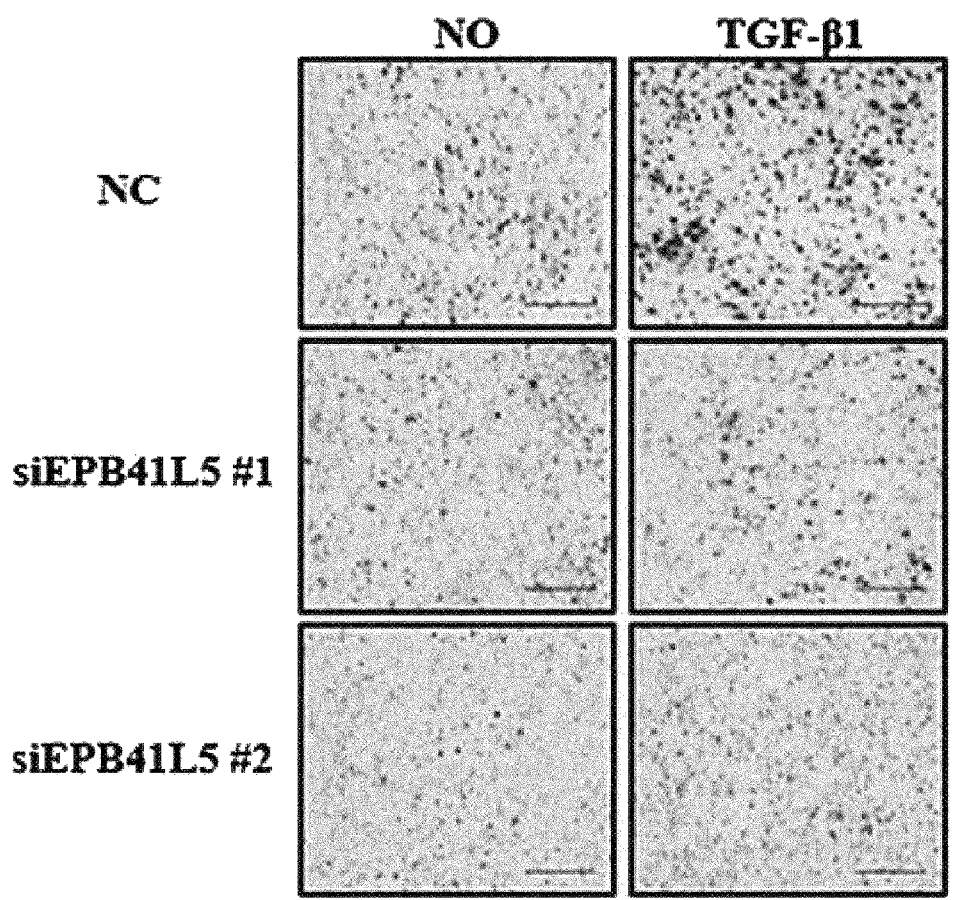
FIG. 5D depicts images showing the results of performing in vitro migration and invasion analysis on NC siRNA-transfected KATOIII cells and EPB41L5 siRNA #1- or EPB41L5 siRNA #2-transfected KATOIII cells depending on the presence or absence of TGF-β1. Scale bars represent 20 μm.

In addition, as a result of analyzing epithelial-mesenchymal transition and the migration of gastric cancer cells when the KATOIII cells transfected with NC siRNA and the KATOIII cells transfected with EPB41L5 siRNA #1 or EPB41L5 siRNA #2 were treated with TGF-β1, it was confirmed that knockdown of EPB41L5 blocked the effect of TGF-β1 on epithelial-mesenchymal transition and the migration of gastric cancer cells (FIGS. 5C, 5D and 5E). That is, it can be seen that EPB41L5 is an essential element for cell metastasis and gastric cancer cell migration which are induced by TGFβ.

<Example 6>. Anti-EPB41L5 mAb (Monoclonal Antibody) Recognizes 619-624 AA Sequence of C-Terminus In the present disclosure, it was considered that, since cell adhesion molecules play an important role in metastasis, it is possible to develop new therapeutic agents using monoclonal antibodies and peptides. Thus, a monoclonal antibody (mAb) against EPB41L5 was developed.

Figure 6C:
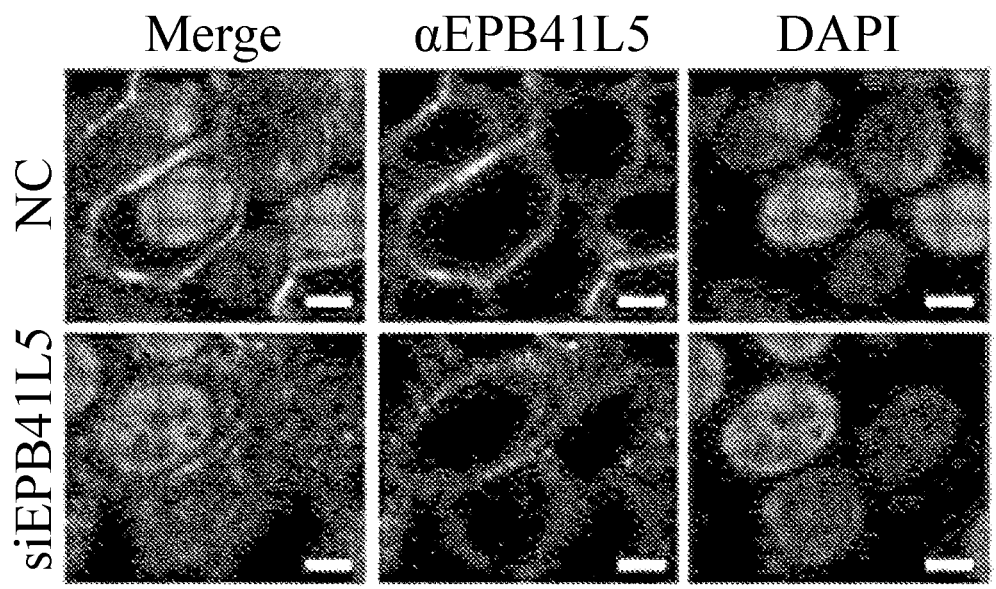
Figure 6D:
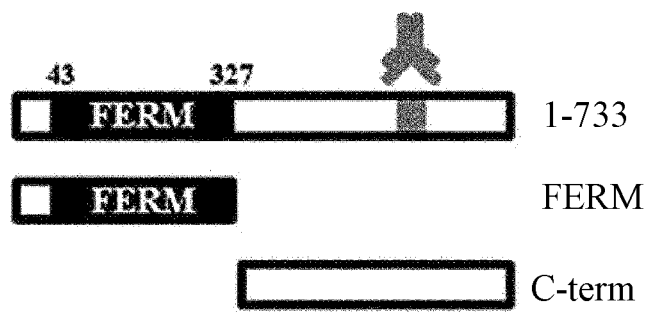
Figure 6E:
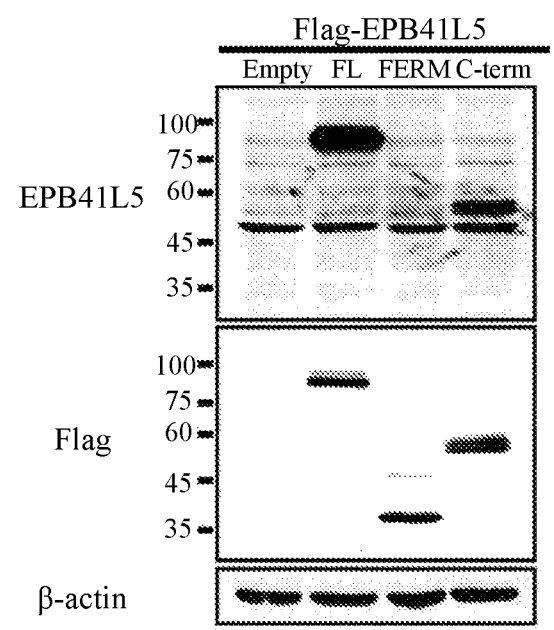

To validate the specificity of the developed antibody, gastric cancer cells transfected with Flag-EPB41L5 or EPB41L5 siRNA were analyzed by Western blot analysis and immunofluorescence analysis. As a result, it was confirmed that overexpressed EPB41L5 was detected in the gastric cancer cells transfected with Flag-EPB41L5 (FIG. 6A), and that EPB41L5 was silenced in the gastric cancer cells (NC, siRNA #1 or siRNA #2) transfected with EPB41L5 siRNA (FIG. 6B). In addition, as a result of analyzing the EPB41L5 siRNA-transfected gastric cancer cells by immunofluorescent staining, it can be seen that EPB41L5 was apparently detected by the anti-EPB41L5 monoclonal antibody in the gastric cancer cells (FIG. 6C). As a result of analyzing the anti-EPB41L5 monoclonal antibody in the present disclosure by Western blot analysis, it was confirmed that the anti-EPB41L5 monoclonal antibody recognized the C-terminus of EPB41L5, not the N-terminal FERM domain of EPB41L5 (FIGS. 6D and 6 #).

Figure 6F:
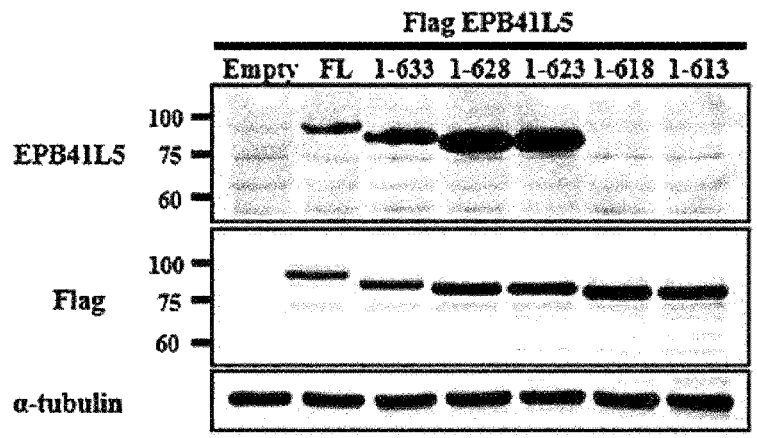
Figure 6G:
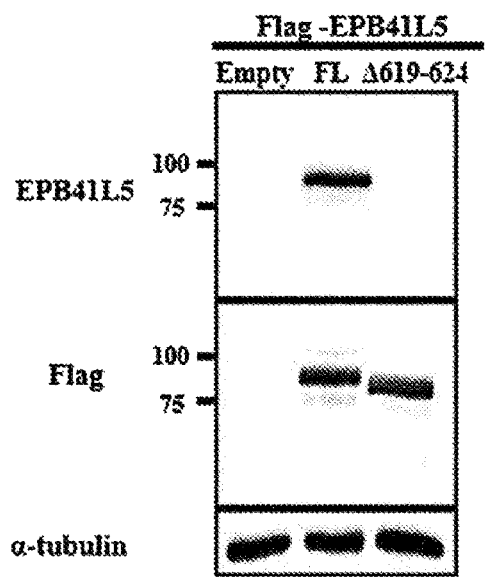
Figure 6H:
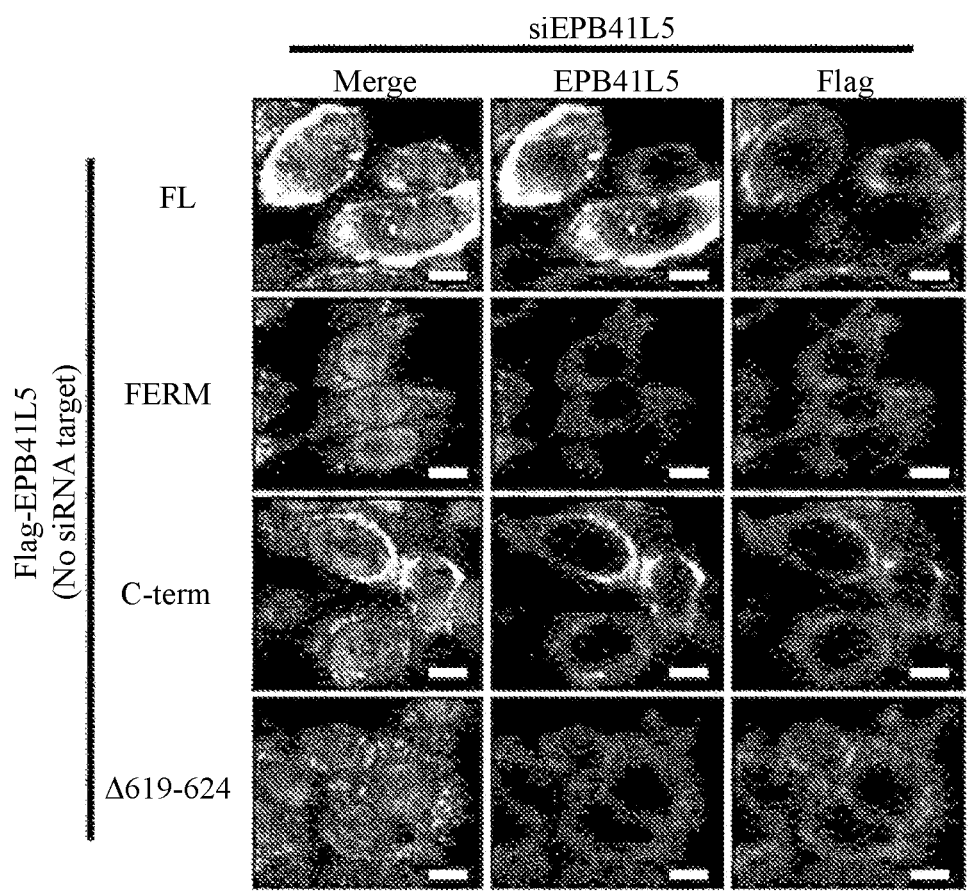

In addition, as a result of analyzing the antibodies in which 5 amino acids at the C-terminus of EPB41L5 were sequentially removed, it was confirmed that the antibodies recognized amino acids 619-624 of the C-terminus of EPB41L5 (FIGS. 6F and 6G). Considering the characteristics of nonpermeabilized immunofluorescent staining, in order to inhibit expression of endogenous EPB41L5, cells were co-transfected with EPB41L5 siRNA and any one plasmid selected from among FL (full length) of EPB41L5, FERM of EPB41L5, C-terminus of EPB41L5 and A619-624 of EPB41L5. Then, expression of exogenous EPB41L5 was analyzed using anti-Flag antibody. EPB41L5 expression was detected in FK cells transfected with FL and C-terminal constructs and in MKN28 cells not transfected with A619-624 (FIG. 6H). Taking these results together, it can be seen that the anti-EPB41L5 monoclonal antibody specifically recognizes the 619-624 amino acid region of EPB41L5.

<Example 7>. Sequencing of Variable Region of Anti-EPB41L5 Monoclonal Antibody

The sequence of the variable region of the monoclonal antibody produced Example 6 above was analyzed by ATgen (Korea). As a result, the sequences of the heavy-chain variable region and light-chain variable region of the monoclonal antibody according to the present disclosure are as follows:
Heavy-Chain Variable Region (SEQ ID NO: 12)
QVQLKESGTVLARPGASVKMSCKASGYTFTSYWMHWVKQRPGQGLEWIG

AIYPGNSDTSYNQKFKDKAKLTAVTSTSTAYMELSSLTDEASAVYYCTR

GGKLPFAMDYWGQGTSVTVSS

Light-Chain Variable Region (SEQ ID NO: 13)
DVLMTQTPLSLPVSLGDQASMSCRSSQSLVHSNGNTYLHWYLQKPGQSP

KLLIYKVSNRFSGVPDRFSGSGSGTDFTLKISRVEAEDLGVYFCSQSTH

VPWTFGGGTKLEIK

Furthermore, the sequences of the heavy-chain variable region CDR1 to CDR3 and light-chain variable region CDR1 to CDR3 of the monoclonal antibody according to the present disclosure are as follows:
   Heavy-chain variable region CDR1: Gly Tyr Thr Phe Thr Ser Tyr Trp (SEQ ID NO: 6)
   Heavy-chain variable region CDR2: Ile Tyr Pro Gly Asn Ser Asp (SEQ ID NO: 7)
   Heavy-chain variable region CDR3: Thr Arg Gly Gly Lys Leu Pro Phe Ala Met Asp Tyr (SEQ ID NO: 8)
   Light-chain variable region CDR1: Gln Ser Leu Val His Ser Asn Gly Asn Thr Tyr (SEQ ID NO: 9)
   Light-chain variable region CDR2: Lys Val Ser (SEQ ID NO: 10)
   Light-chain variable region CDR3: Ser Gln Ser Thr His Val Pro Trp Thr (SEQ ID NO: 11)

<Example 8>. Therapeutic Effect of Anti-EPB41L5 Monoclonal Antibody

Figure 7A:
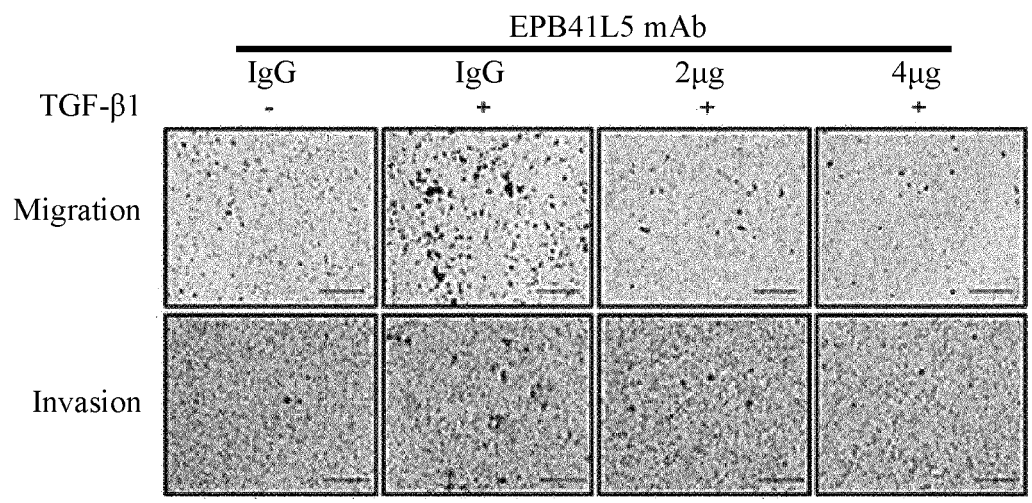
FIG. 7A depicts cell migration images and FIG. 7B depicts an analysis result graph, obtained by treating KATOIII cells with various concentrations of anti-EPB41L5 mAb depending on the presence or absence of TGF-β1 in order to confirm that the invasion and metastasis of gastric cancer cells that was increased by TGF-β1 is inhibited by an anti-EPB41L5 monoclonal antibody. Experimental data are expressed as mean s.e.m, and scale bars represent 20 μm. P<0.01 and *P<0.001.
Figure 7B:
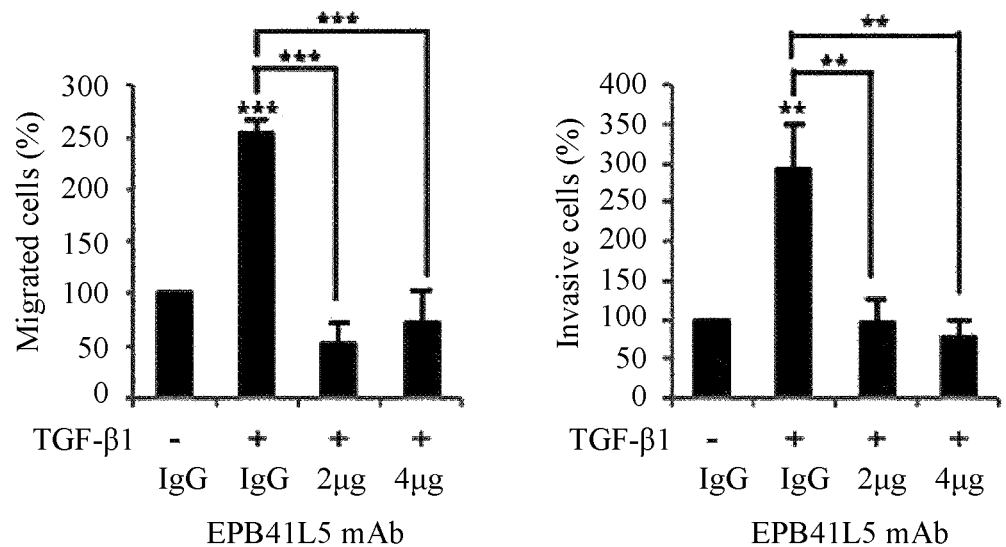

The specificity of the anti-EPB41L5 monoclonal antibody was validated. In this experiment, as a result of evaluating the effect of the anti-EPB41L5 monoclonal antibody on the migration of gastric cancer (GC) cells with or without TGF-β1 treatment, it was confirmed that TGF-β1 efficiently increased the migration of KATOIII. Furthermore, it was confirmed that the anti-EPB41L5 monoclonal antibody inhibited the migration of KATOIII cells that was increased by TGF-β1 (FIGS. 7A and 7B).

Figure 8:
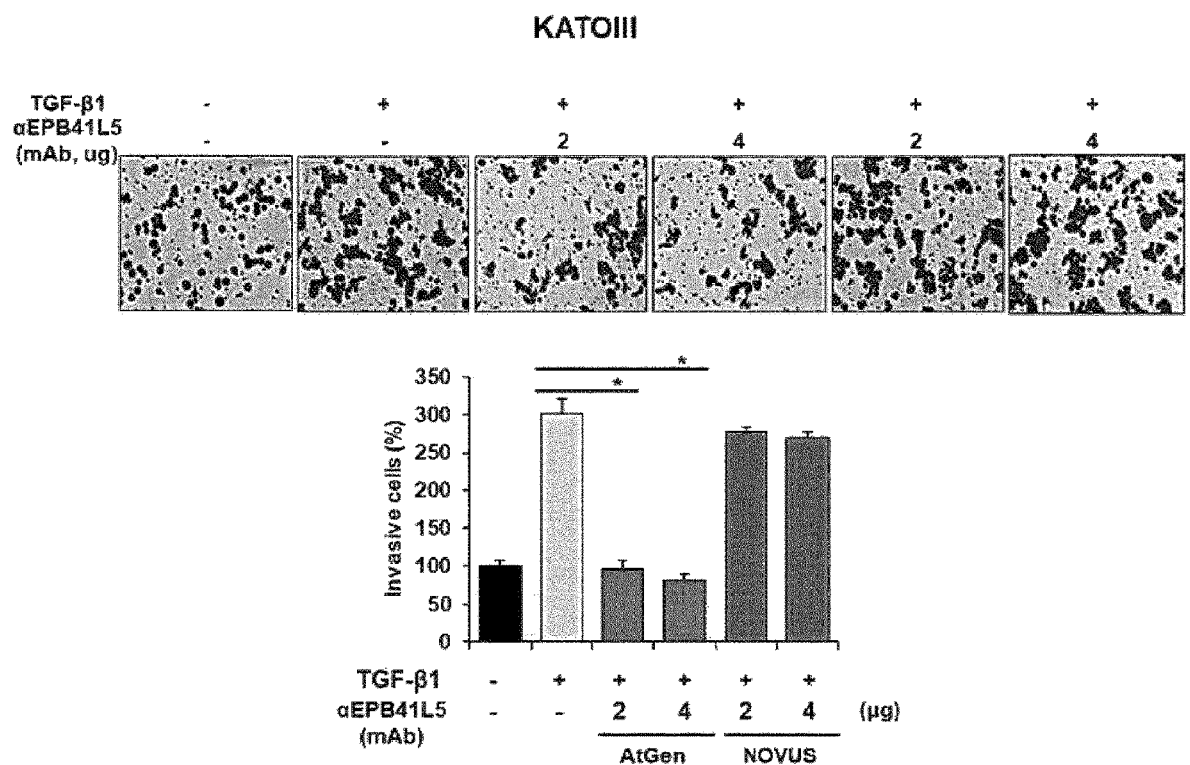
FIG. 8 shows the results of comparing the degree to which the invasion and metastasis of gastric cancer cells that was increased by TGF-β1 is inhibited by an anti-EPB41L5 monoclonal antibody, between the monoclonal antibody of the present disclosure and an antibody that recognizes other epitopes.

<Example 9>. Comparison of Metastasis Inhibitory Effect of Anti-EPB41L5 Monoclonal Antibody In the same manner as in Example 8, the degree of cell migration inhibited by the anti-EPB41L5 monoclonal antibody was compared between different epitope sequences recognized by the monoclonal antibody. As shown in FIG. 8, it was confirmed that the monoclonal antibody (AtGen) according to the present disclosure significantly (100%) inhibited cell migration that was increased by TGF-β1, whereas an antibody (Novus antibody) recognizing the $638^{th}$ to $708^{th}$ amino acid sequence of EPB41L5 protein hardly inhibited cell migration that was increased by TGF-β1. Accordingly, it can be seen that the antibody recognizing the $619^{th}$ to $624^{t}$ amino acid sequence of the C-terminal region of EPB41L5 can very effectively inhibit cell migration, which was increased by TGF-β1, compared to antibodies that bind specifically to epitopes consisting of other amino acid sequences.

<Example 10>. Analysis of Relevance of EPB41L5 with Gastric Cancer Cell Metastasis Through the above-described experiments, it was confirmed that EPB41L5 expression, which was increased by TGF-β1, is involved in the in vivo migration and invasion of gastric cancer cells. Accordingly, in the present disclosure, the effect of EPB41L5 on the migration of gastric cancer cells was analyzed by in vitro migration and invasion assay.

Specifically, EPB41L5-overexpressing KATOIII cells and untreated KATOIII cells as a vehicle were prepared.

Figure 9A:
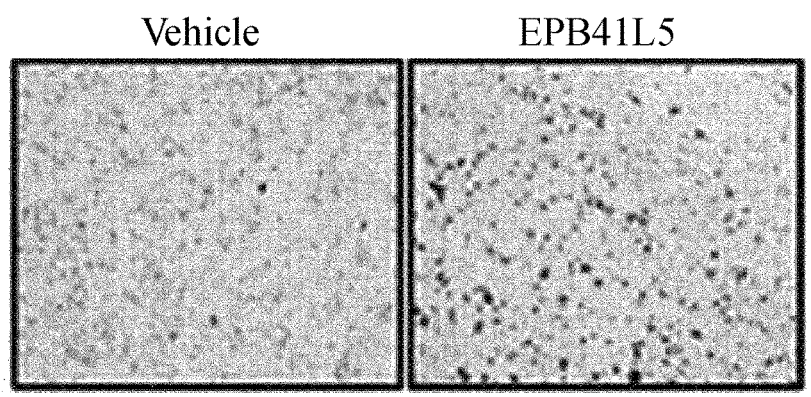
FIGS. 9A-9D show the results of an experiment performed to confirm the relevance of EPB41L5 with the lung metastasis of gastric cancer cells.
Figure 9B:
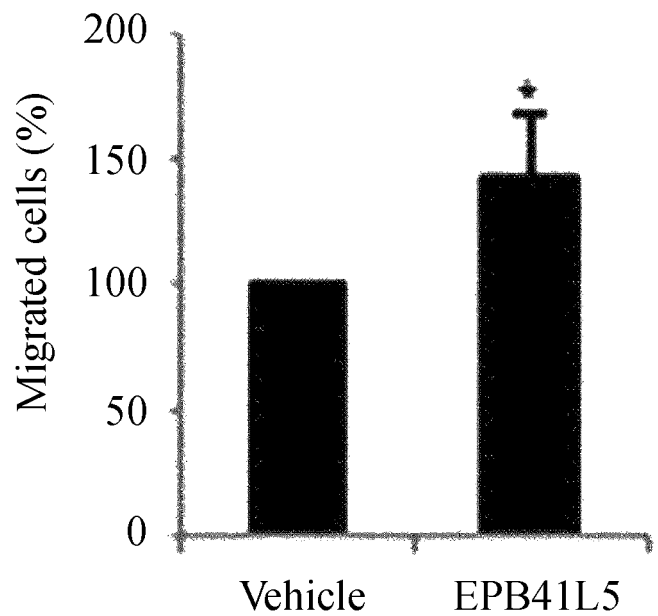
Figure 9C:
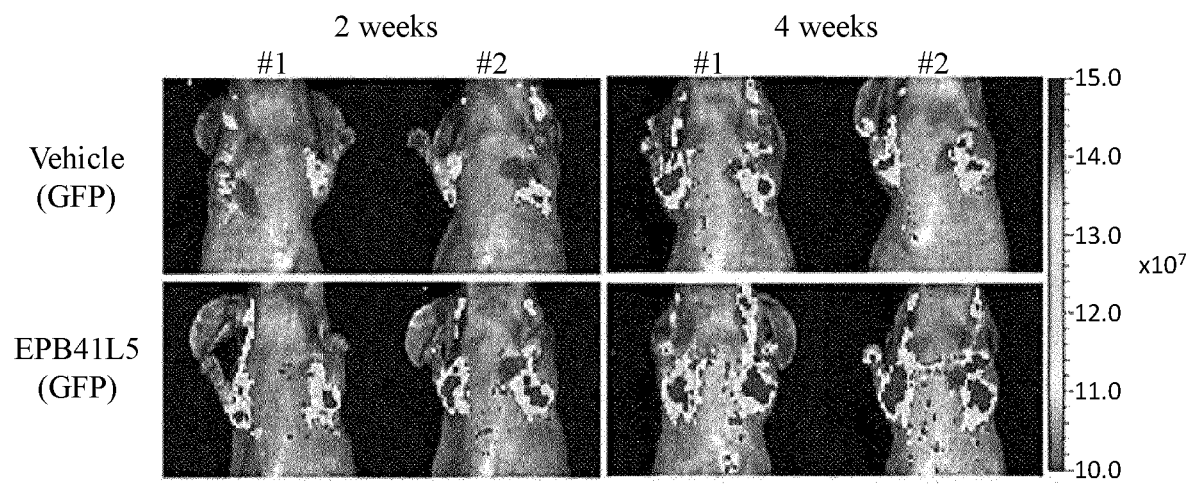
Figure 9D:
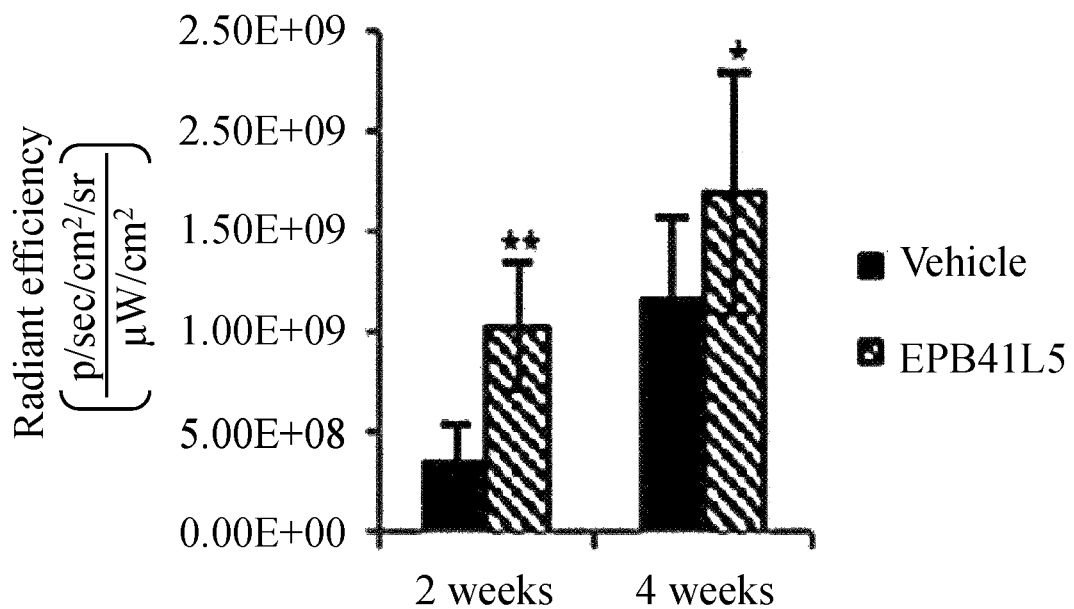

As a result of analyzing in vitro migration and invasion assay in EPB41L5-verexpressing KATOIII cells, it was confirmed that the migration and invasion of the EPB41L5-overexpressing KATOIII cells substantially increased (FIGS. 9A and 9B). To observe the effect of in vivo EPB41L5 expression on gastric cancer cells, EPB41L5-overexpressing KATOIII cells were injected into nude mice through the tail vein. As a result, it was confirmed that the lung metastasis of gastric cancer cells in the EPB41L5(GFP) group significantly increased compared to that in the vehicle (GFP) group (FIGS. 9C and 9D). In summary, it can be seen that EPB41L5 promotes in vivo metastasis of gastric cancer cells.

Figure 10A:
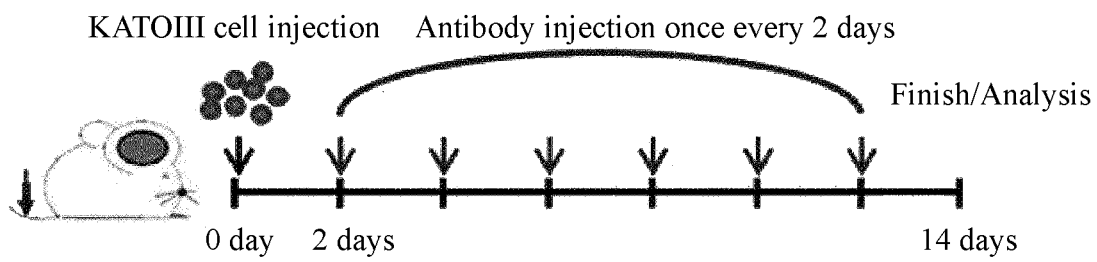
FIG. 10A is a diagram showing that a (EPB41L5+mAb) group is prepared by injecting EPB41L5-overexpressing KATOIII cells into nude mice through the tail vein and injecting an anti-EPB41L5 monoclonal antibody into the mice at a dose of 5 mg/kg once every 2 days for 2 weeks.

<Example 11>. Examination of Ability of Anti-EPB41L5 Monoclonal Antibody to Inhibit Metastasis of Gastric Cancer Cells The in vivo efficacy of the anti-EPB41L5 monoclonal antibody was examined. To this end, the following groups were prepared: a vehicle group; an (EPB41L5) group obtained by injecting EPB41L5-overexpressing KATOIII cells into nude mice through the tail vein; and an (EPB41L5+mAb) group obtained by injecting EPB41L5-overexpressing KATOIII cells into nude mice through the tail vein and 5 mg/kg of the anti-EPB41L5 monoclonal antibody into the nude mice once every 2 days for 2 weeks (FIG. 10A).

Figure 10B:
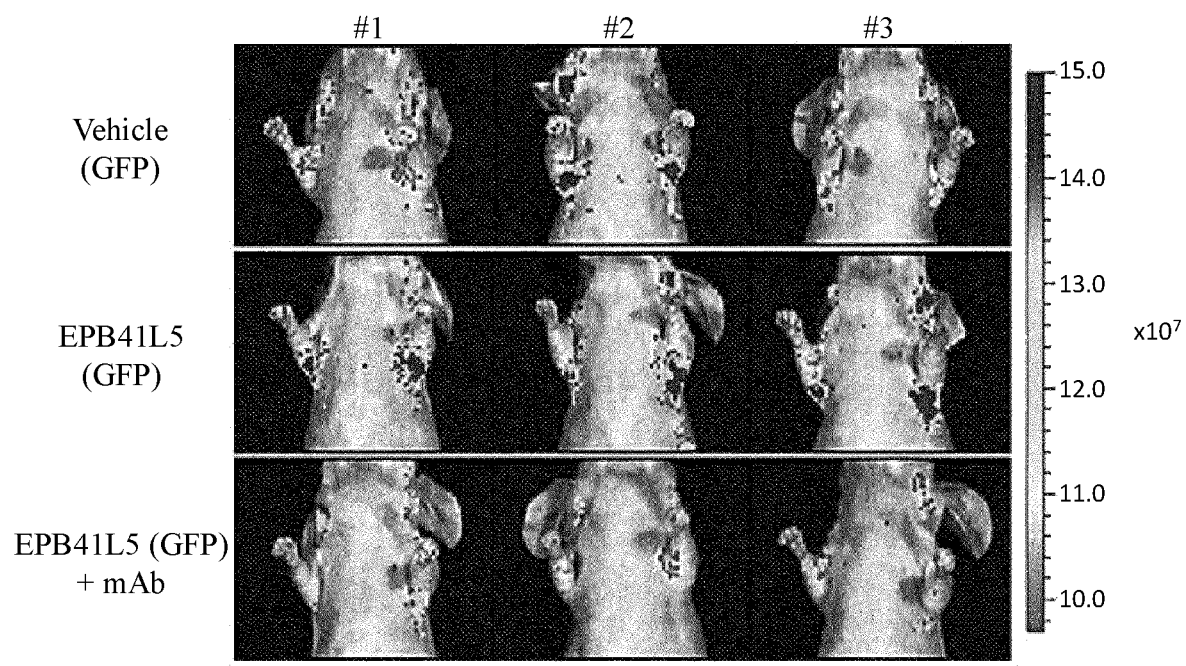
FIG. 10B shows the results of analyzing a control group (vehicle), an (EPB41L5) group obtained by injecting EPB41L5-overexpressing KATOIII cells into nude mice through the tail vein, and an (EPB41L5+mAb) group obtained by injecting EPB41L5-overexpressing $KATO^2$ cells into nude mice through the tail vein and injecting an anti-EPB41L5 monoclonal antibody into the mice at a dose of 5 mg/ml once every 2 days for 2 weeks, by an IVIS optical imaging system.
Figure 10C:
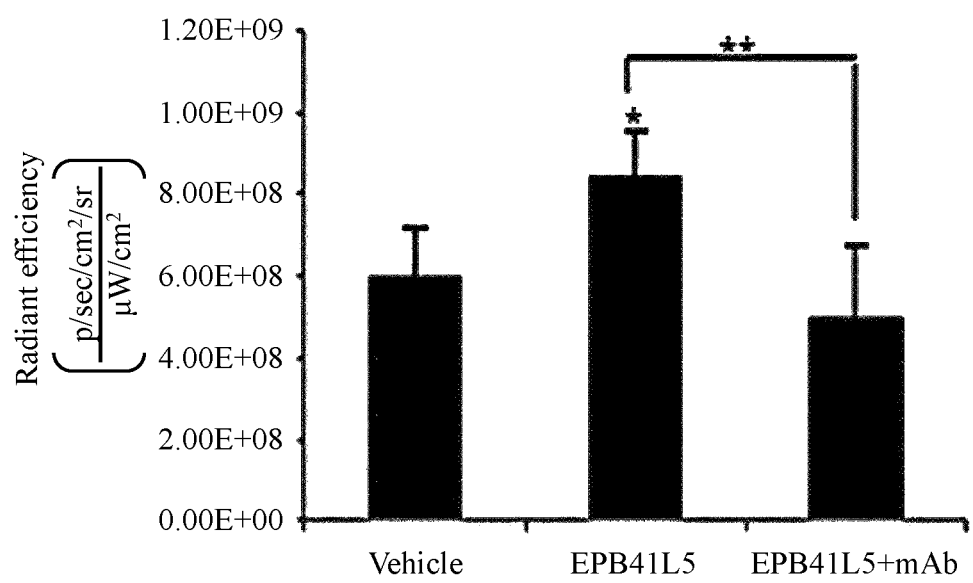
FIG. 10C is a graph showing the results of quantifying intensity from the images of FIG. 9B by an ROI tool. Experimental data are expressed as average radiant efficiency±s.e.m. **P<0.01.

It can be confirmed that, in the nude mice into which the EPB41L5-overexpressing cells were injected, the lung metastasis of cancer increased, but in the group into which the anti-EPB41L5 monoclonal antibody was injected, the lung metastasis of gastric cancer cells decreased compared to that in the vehicle group (FIGS. 10B and 10C). Thereby, it can be seen that the anti-EPB41L5 monoclonal antibody according to the present disclosure exhibits therapeutic or preventive effects against advanced gastric cancer.

<Example 12>. Confirmation of Function of Anti-EPB41L5 Monoclonal Antibody That Specifically Recognizes EBP41L5 Protein The specificity of the anti-EPB41L5 monoclonal antibody to EBP41L5 was confirmed. To this end, KATOIII cells and MKN28 cells were prepared as gastric cancer cell lines. As lung cancer cell lines, A549 cells and H226 cells were prepared, and as breast cancer cell lines, MCF7 cells and MDA-MB-231 cells were prepared. The cells were obtained from Professor Cheong Jae-Ho lab at Yonsei University and from the Korean Cell Line Bank. Each cell line was cultured in RPMI-1640 medium supplemented with 10% FBS and 1% antibiotic/antimycotic solution (Corning, Manassas, VA, USA)) at 37° C. under 5% $CO_2$.

Figure 11:
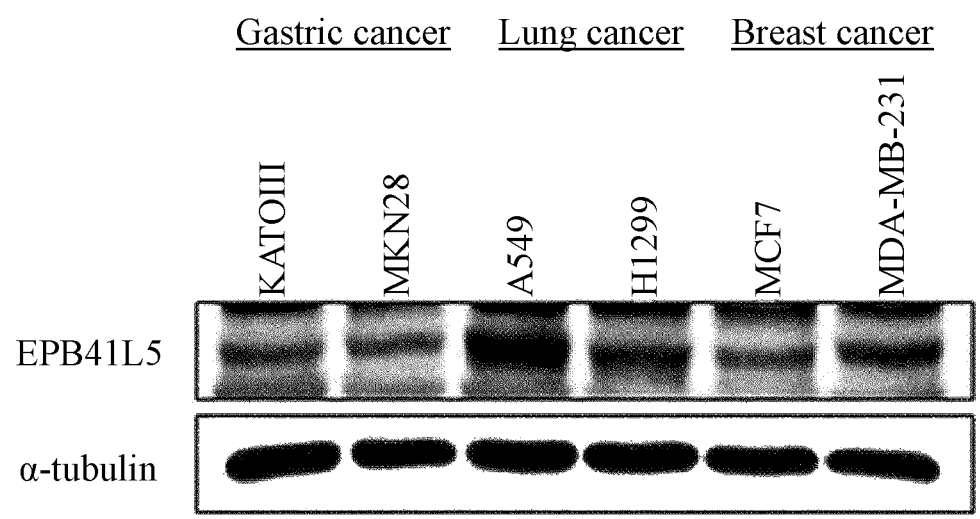
FIG. 11 shows the results of analyzing the expression and antibody function of EBP41L5 protein in gastric cancer, lung cancer and breast cancer cells by Western blot analysis using an EPB41L5 antibody.

Using the anti-EPB41L5 monoclonal antibody, EBP41L5 protein expression in each cell group was analyzed by Western blot analysis (FIG. 11). As a result, EBP41L5 protein expression was detected by the anti-EPB41L5 monoclonal antibody not only in the gastric cancer cell lines but also in the lung cancer cell lines and the breast cancer cell lines (FIG. 11). This indicates that the anti-EPB41L5 monoclonal antibody according to the present disclosure may be effectively used for treatment or prevention of not only gastric cancer but also lung cancer and breast cancer.

<Example 13>. Examination of Cell-Specific Toxicity of Anti-EPB41L5 Monoclonal Antibody The effects of the anti-EPB41L5 monoclonal antibody of the present disclosure on the cell viabilities of various cells were examined. To this end, KATOIII cells and MKN28 cells were prepared as gastric cancer cell lines. As lung cancer cell lines, A549 cells and H226 cells were prepared, and as breast cancer cell lines, MCF7 cells and MDA-MB-231 cells were prepared. The cells were obtained from Professor Cheong Jae-Ho lab at Yonsei University and from the Korean Cell Line Bank.

Each cell line was cultured in RPMI-1640 medium supplemented with 10% FBS and 1% antibiotic/antimycotic solution (Corning, Manassas, VA, USA)) at 37° C. under 5% $CO_2$.

Figure 12:
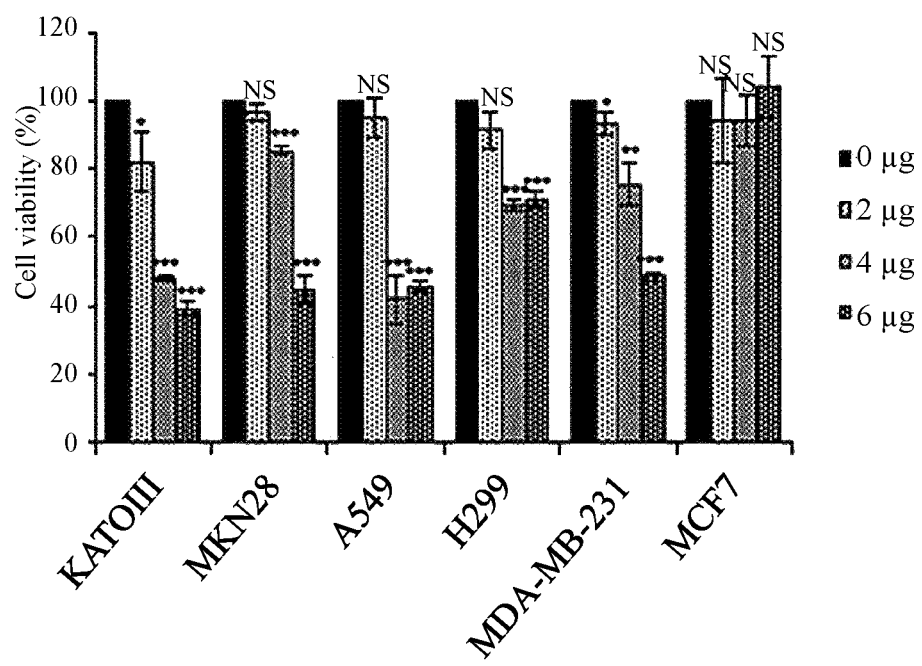
FIG. 12 is a graph showing the results of analyzing the cell viabilities of gastric cancer, lung cancer and breast cancer cells treated with various concentrations of an EBP41L5 antibody.

0, 2, 4 or 6 μg of the anti-EPB41L5 monoclonal antibody was injected into each cell group, and after 24 hours, the cell viability (%) of each cell group was analyzed by a 3-[4,5-dimethylthiazol-2-yl]-2,5-diphenyltertrazolium bromide (MTT) reduction method (FIG. 12). As a result, it was confirmed that, when the anti-EPB41L5 monoclonal antibody was injected, the cell viability decreased in a concentration-dependent manner, suggesting that the anti-EPB41L5 monoclonal antibody of the present disclosure exhibits therapeutic or preventive effects against advanced cancer or gastric cancer (FIG. 12).

CONCLUSION

Cell adhesion proteins play a critical role in cancer metastasis. Accordingly, the possibility of developing therapeutic agents against cancer metastasis using antibodies against cell adhesion proteins has been discussed. The present inventors have made efforts to develop a new therapy based on a new adhesion molecule or complex related to metastasis, thereby completing the present disclosure. In EMT (Epithelial to Mesenchymal Transition), epithelial cells lose cell-cell junctions and cell polarity, and the actin cytoskeleton is reorganized to enable the mesenchymal phenotype. EPB41L5 is reported to interact with p120-catenin, which destabilizes E-cadherin, and paxillin, a focal adhesion kinase. In addition, it is known that EPB41L5 binds to MPP5, a Crumbs complex component that negatively regulates cell polarity. Another junction protein, β-catenin, colocalizes with EPB41L5 in the basolateral membrane of kidney epithelial cells, but its binding has not been confirmed. FAK has an FERM domain in its N-terminus and binds with ASAP1/AMAP1 and paxillin, another binding partner of EPB41L5 in the C-terminus.

In the present disclosure, it has been found that EPB41L5 is responsible for the poor prognosis of gastric cancer patients. In this regard, it was demonstrated that EPB41L5 is highly expressed in cancer cells. Meanwhile, since TGFβ is known to promote gastric cancer metastasis, it was predicted that expression of TGFβ would have relevance to lymph node metastasis and the prognosis of cancer. As a result of analyzing the relevance between TGFβ and EPB41L5, a large number of Smad-binding motifs were identified on the EPB41L5 gene promoter.

Accordingly, it was confirmed that knockdown of EPB41L5 abrogates the TGFβ1-induced increases in mesenchymal transition and GC cell migration, indicating that EPB41L5 is a major factor in TGFβ signaling. Taking these results together, it can be seen that knockdown of EPB41L5 can control the migration and invasion of gastric cancer cells caused by epithelial-mesenchymal transition through the TGFβ/Smad3/EPB41L5 pathway.

In the present disclosure, it was confirmed that EPB41L5 is located on the cell surface and promotes the in vitro and in vivo metastasis of gastric cancer cells, suggesting that an antibody that binds specifically to EPB41L5 may be used as a therapeutic monoclonal antibody. Accordingly, the EPB41L5 monoclonal antibody was developed. It was confirmed that the EPB41L5 monoclonal antibody effectively blocked the TGF-β1-induced migration and invasion of gastric cancer cells, and that increased lung metastasis of EPB41L5-overexprressing cells was significantly inhibited by the anti-EPB41L5 monoclonal antibody.

In addition, it was confirmed that the anti-EPB41L5 monoclonal antibody of the present disclosure significantly inhibited EPB41L5 protein expression in each of gastric cancer, lung cancer and breast cancer cell lines (in particular, gastric cancer cell line) and decreased the viability of cancer cells.

Therefore, it can be seen that the EPB41L5 monoclonal antibody of the present disclosure is a very effective method for prevention, treatment, or inhibition of metastasis, of cancer, particularly gastric cancer.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto.

INDUSTRIAL APPLICABILITY

The features and advantages of the present disclosure are summarized as follows:

(1) The present disclosure provides a monoclonal antibody and a fragment thereof that recognizes EPB41L5 as an antigen and binds specifically thereto.

(2) The present disclosure may be used to identify an antibody that binds specifically to an epitope of EPB41L5, and an antibody identified through this method functions to inhibit EPB41L5 signaling and, and this function enables the antibody to be effectively used as a vaccine or therapeutic agent against cancer in which EPB41L5 is involved, particularly gastric cancer.

The invention claimed is:

1. A monoclonal antibody or a fragment thereof which recognizes an EPB41L5 protein comprising the amino acid sequence of SEQ ID NO: 1 as an antigen and binds specifically thereto, wherein the monoclonal antibody or the fragment thereof binds to an epitope consisting of $619^{th}$ to $624^{th}$ amino acid residues of the EPB41L5 protein comprising the amino acid sequence of SEQ ID NO: 1, the monoclonal antibody or the fragment thereof comprising: a heavy-chain variable region comprising a heavy-chain CDR1 comprising SEQ ID NO: 6, a heavy-chain CDR2 comprising SEQ ID NO: 7, and a heavy-chain CDR3 comprising SEQ ID NO: 8, and a light-chain variable region comprising a light-chain CDR1 comprising SEQ ID NO: 9, a light-chain CDR2 comprising SEQ ID NO: 10, and a light-chain CDR3 comprising SEQ ID NO: 11.

2. The monoclonal antibody or fragment thereof of claim 1, which blocks interaction between EPB41L5 and TGF-β1.

3. The monoclonal antibody or fragment thereof of claim 1, wherein the antibody is a chimeric antibody, a humanized antibody, a bivalent-bispecific molecule, a minibody, a bispecific antibody, an antibody mimic, a diabody, a triabody, a tetrabody, or a fragment thereof.

4. A nucleic acid molecule encoding the monoclonal antibody or fragment thereof of claim 1.

5. A vector comprising the nucleic acid molecule of claim 4.

6. A host cell comprising the vector of claim 5.

7. A pharmaceutical composition for treating a cancer expressing EPB41L5, the pharmaceutical composition containing, as an active ingredient, at least any one selected from the group consisting of: the monoclonal antibody or fragment thereof of claim 1; a nucleic acid molecule encoding the monoclonal antibody or fragment thereof; or a vector comprising the nucleic acid molecule.

8. A method for treating a cancer expressing EPB41L5, the method comprising administering to a patient with the cancer expressing EPB41L5 the pharmaceutical composition according to claim 7.

* * * * *

SEQUENCE LISTING

```
<160> NUMBER OF SEQ ID NOS: 27

<210> SEQ ID NO 1
<211> LENGTH: 733
<212> TYPE: PRT
<213> ORGANISM: Artificial Sequence
<220> FEATURE:
<223> OTHER INFORMATION: EPB41L5 protein

<400> SEQUENCE: 1

Met Leu Ser Phe Phe Arg Arg Thr Leu Gly Arg Arg Ser Met Arg Lys
1               5                   10                  15

His Ala Glu Lys Glu Arg Leu Arg Glu Ala Gln Arg Ala Ala Thr His
            20                  25                  30

Ile Pro Ala Ala Gly Asp Ser Lys Ser Ile Ile Thr Cys Arg Val Ser
        35                  40                  45

Leu Leu Asp Gly Thr Asp Val Ser Val Asp Leu Pro Lys Lys Ala Lys
    50                  55                  60

Gly Gln Glu Leu Phe Asp Gln Ile Met Tyr His Leu Asp Leu Ile Glu
65                  70                  75                  80

Ser Asp Tyr Phe Gly Leu Arg Phe Met Asp Ser Ala Gln Val Ala His
                85                  90                  95

Trp Leu Asp Gly Thr Lys Ser Ile Lys Lys Gln Val Lys Ile Gly Ser
            100                 105                 110

Pro Tyr Cys Leu His Leu Arg Val Lys Phe Tyr Ser Ser Glu Pro Asn
        115                 120                 125

Asn Leu Arg Glu Glu Leu Thr Arg Tyr Leu Phe Val Leu Gln Leu Lys
    130                 135                 140

Gln Asp Ile Leu Ser Gly Lys Leu Asp Cys Pro Phe Asp Thr Ala Val
145                 150                 155                 160

Gln Leu Ala Ala Tyr Asn Leu Gln Ala Glu Leu Gly Asp Tyr Asp Leu
                165                 170                 175

Ala Glu His Ser Pro Glu Leu Val Ser Glu Phe Arg Phe Val Pro Ile
            180                 185                 190

Gln Thr Glu Glu Met Glu Leu Ala Ile Phe Glu Lys Trp Lys Glu Tyr
        195                 200                 205

Arg Gly Gln Thr Pro Ala Gln Ala Glu Thr Asn Tyr Leu Asn Lys Ala
    210                 215                 220

Lys Trp Leu Glu Met Tyr Gly Val Asp Met His Val Val Lys Ala Arg
225                 230                 235                 240
```

-continued

```
Asp Gly Asn Asp Tyr Ser Leu Gly Leu Thr Pro Thr Gly Val Leu Val
            245                 250                 255
Phe Glu Gly Asp Thr Lys Ile Gly Leu Phe Phe Trp Pro Lys Ile Thr
                260                 265                 270
Arg Leu Asp Phe Lys Lys Asn Lys Leu Thr Leu Val Val Glu Asp
            275                 280                 285
Asp Asp Gln Gly Lys Glu Gln Glu His Thr Phe Val Phe Arg Leu Asp
            290                 295                 300
His Pro Lys Ala Cys Lys His Leu Trp Lys Cys Ala Val Glu His His
305                 310                 315                 320
Ala Phe Phe Arg Leu Arg Gly Pro Val Gln Lys Ser Ser His Arg Ser
                325                 330                 335
Gly Phe Ile Arg Leu Gly Ser Arg Phe Arg Tyr Ser Gly Lys Thr Glu
                340                 345                 350
Tyr Gln Thr Thr Lys Thr Asn Lys Ala Arg Arg Ser Thr Ser Phe Glu
            355                 360                 365
Arg Arg Pro Ser Lys Arg Tyr Ser Arg Arg Thr Leu Gln Met Lys Ala
            370                 375                 380
Cys Ala Thr Lys Pro Glu Glu Leu Ser Val His Asn Asn Val Ser Thr
385                 390                 395                 400
Gln Ser Asn Gly Ser Gln Gln Ala Trp Gly Met Arg Ser Ala Leu Pro
                405                 410                 415
Val Ser Pro Ser Ile Ser Ser Ala Pro Val Pro Val Glu Ile Glu Asn
                420                 425                 430
Leu Pro Gln Ser Pro Gly Thr Asp Gln His Asp Arg Lys Cys Ile Pro
            435                 440                 445
Leu Asn Ile Asp Leu Leu Asn Ser Pro Asp Leu Leu Glu Ala Thr Ile
450                 455                 460
Gly Asp Val Ile Gly Ala Ser Asp Thr Met Glu Thr Ser Gln Ala Leu
465                 470                 475                 480
Asn Asp Val Asn Val Ala Thr Arg Leu Pro Gly Leu Gly Glu Pro Glu
                485                 490                 495
Val Glu Tyr Glu Thr Leu Lys Asp Thr Ser Glu Lys Leu Lys Gln Leu
            500                 505                 510
Glu Met Glu Asn Ser Pro Leu Leu Ser Pro Arg Ser Asn Ile Asp Val
            515                 520                 525
Asn Ile Asn Ser Gln Glu Glu Val Val Lys Leu Thr Glu Lys Cys Leu
530                 535                 540
Asn Asn Val Ile Glu Ser Pro Gly Leu Asn Val Met Arg Val Pro Pro
545                 550                 555                 560
Asp Phe Lys Ser Asn Ile Leu Lys Ala Gln Val Glu Ala Val His Lys
                565                 570                 575
Val Thr Lys Glu Asp Ser Leu Leu Ser His Lys Asn Ala Asn Val Gln
            580                 585                 590
Asp Ala Ala Thr Asn Ser Ala Val Leu Asn Glu Asn Asn Val Pro Leu
            595                 600                 605
Pro Lys Glu Ser Leu Glu Thr Leu Met Leu Ile Thr Pro Ala Asp Ser
610                 615                 620
Gly Ser Val Leu Lys Glu Ala Thr Asp Glu Leu Asp Ala Leu Leu Ala
625                 630                 635                 640
Ser Leu Thr Glu Asn Leu Ile Asp His Thr Val Ala Pro Gln Val Ser
                645                 650                 655
```

```
Ser Thr Ser Met Ile Thr Pro Arg Trp Ile Val Pro Gln Ser Gly Ala
            660                 665                 670

Met Ser Asn Gly Leu Ala Gly Cys Glu Met Leu Leu Thr Gly Lys Glu
        675                 680                 685

Gly His Gly Asn Lys Asp Gly Ile Ser Leu Ile Ser Pro Pro Ala Pro
    690                 695                 700

Phe Leu Val Asp Ala Val Thr Ser Ser Gly Pro Ile Leu Ala Glu Glu
705                 710                 715                 720

Ala Val Leu Lys Gln Lys Cys Leu Leu Thr Thr Glu Leu
                725                 730

<210> SEQ ID NO 2
<211> LENGTH: 6
<212> TYPE: PRT
<213> ORGANISM: Artificial Sequence
<220> FEATURE:
<223> OTHER INFORMATION: EPB41L5 epitope

<400> SEQUENCE: 2

Ile Thr Pro Ala Asp Ser
1               5

<210> SEQ ID NO 3
<211> LENGTH: 270
<212> TYPE: PRT
<213> ORGANISM: Artificial Sequence
<220> FEATURE:
<223> OTHER INFORMATION: Human EPB41L5 antigen 386 to 637th amino acid
      residue

<400> SEQUENCE: 3

Glu Arg Arg Pro Ser Lys Arg Tyr Ser Arg Arg Thr Leu Gln Met Lys
1               5                   10                  15

Ala Cys Ala Thr Lys Pro Glu Glu Leu Ser Val His Asn Asn Val Ser
            20                  25                  30

Thr Gln Ser Asn Gly Ser Gln Gln Ala Trp Gly Met Arg Ser Ala Leu
        35                  40                  45

Pro Val Ser Pro Ser Ile Ser Ser Ala Pro Val Pro Val Glu Ile Glu
    50                  55                  60

Asn Leu Pro Gln Ser Pro Gly Thr Asp Gln His Asp Arg Lys Cys Ile
65                  70                  75                  80

Pro Leu Asn Ile Asp Leu Leu Asn Ser Pro Asp Leu Leu Glu Ala Thr
                85                  90                  95

Ile Gly Asp Val Ile Gly Ala Ser Asp Thr Met Glu Thr Ser Gln Ala
            100                 105                 110

Leu Asn Asp Val Asn Val Ala Thr Arg Leu Pro Gly Leu Gly Glu Pro
        115                 120                 125

Glu Val Glu Tyr Glu Thr Leu Lys Asp Thr Ser Glu Lys Leu Lys Gln
    130                 135                 140

Leu Glu Met Glu Asn Ser Pro Leu Leu Ser Pro Arg Ser Asn Ile Asp
145                 150                 155                 160

Val Asn Ile Asn Ser Gln Glu Glu Val Val Lys Leu Thr Glu Lys Cys
                165                 170                 175

Leu Asn Asn Val Ile Glu Ser Pro Gly Leu Asn Val Met Arg Val Pro
            180                 185                 190

Pro Asp Phe Lys Ser Asn Ile Leu Lys Ala Gln Val Glu Ala Val His
        195                 200                 205

Lys Val Thr Lys Glu Asp Ser Leu Leu Ser His Lys Asn Ala Asn Val
```

Gln Asp Ala Ala Thr Asn Ser Ala Val Leu Asn Glu Asn Asn Val Pro
225                 230                 235                 240

Leu Pro Lys Glu Ser Leu Glu Thr Leu Met Leu Ile Thr Pro Ala Asp
            245                 250                 255

Ser Gly Ser Val Leu Lys Glu Ala Thr Asp Glu Leu Asp Ala
        260                 265                 270

<210> SEQ ID NO 4
<211> LENGTH: 21
<212> TYPE: RNA
<213> ORGANISM: Artificial Sequence
<220> FEATURE:
<223> OTHER INFORMATION: EPB41L5 siRNA (EPB41L5 siRNA#1)

<400> SEQUENCE: 4
gcaauuggca gcuuauaauu u                                            21

<210> SEQ ID NO 5
<211> LENGTH: 23
<212> TYPE: RNA
<213> ORGANISM: Artificial Sequence
<220> FEATURE:
<223> OTHER INFORMATION: EPB41L5 siRNA (EPB41L5 siRNA#2)

<400> SEQUENCE: 5
uucagauucg ugccuauuca guu                                          23

<210> SEQ ID NO 6
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 6

Gly Tyr Thr Phe Thr Ser Tyr Trp
1               5

<210> SEQ ID NO 7
<211> LENGTH: 7
<212> TYPE: PRT
<213> ORGANISM: Artificial Sequence
<220> FEATURE:
<223> OTHER INFORMATION: Heavy chain CDR2

<400> SEQUENCE: 7

Ile Tyr Pro Gly Asn Ser Asp
1               5

<210> SEQ ID NO 8
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 8

Thr Arg Gly Gly Lys Leu Pro Phe Ala Met Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Light chain CDR1

<400> SEQUENCE: 9

Gln Ser Leu Val His Ser Asn Gly Asn Thr Tyr
1               5                   10

<210> SEQ ID NO 10
<211> LENGTH: 3
<212> TYPE: PRT
<213> ORGANISM: Artificial Sequence
<220> FEATURE:
<223> OTHER INFORMATION: Light chain CDR2

<400> SEQUENCE: 10

Lys Val Ser
1

<210> SEQ ID NO 11
<211> LENGTH: 9
<212> TYPE: PRT
<213> ORGANISM: Artificial Sequence
<220> FEATURE:
<223> OTHER INFORMATION: Light chain CDR3

<400> SEQUENCE: 11

Ser Gln Ser Thr His Val Pro Trp Thr
1               5

<210> SEQ ID NO 12
<211> LENGTH: 119
<212> TYPE: PRT
<213> ORGANISM: Artificial Sequence
<220> FEATURE:
<223> OTHER INFORMATION: Heavy chain_variable region

<400> SEQUENCE: 12

Gln Val Gln Leu Lys Glu Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Lys Asp Lys Ala Lys Leu Thr Ala Val Thr Ser Thr Ser Thr Ala Tyr
65                  70                  75                  80

Met Glu Leu Ser Ser Leu Thr Asp Glu Ala Ser Ala Val Tyr Tyr Cys
                85                  90                  95

Thr Arg Gly Gly Lys Leu Pro Phe Ala Met Asp Tyr Trp Gly Gln Gly
            100                 105                 110

Thr Ser Val Thr Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Light chain_variable region

<400> SEQUENCE: 13

Asp Val Leu Met Thr Gln Thr Pro Leu Ser Leu Pro Val Ser Leu Gly

```
            1               5              10              15
Asp Gln Ala Ser Met Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110

<210> SEQ ID NO 14
<211> LENGTH: 21
<212> TYPE: RNA
<213> ORGANISM: Artificial Sequence
<220> FEATURE:
<223> OTHER INFORMATION: Smad4-1 siRNA

<400> SEQUENCE: 14
gcuacuuacc aucauaacau u                                              21

<210> SEQ ID NO 15
<211> LENGTH: 23
<212> TYPE: RNA
<213> ORGANISM: Artificial Sequence
<220> FEATURE:
<223> OTHER INFORMATION: Smad4-2 siRNA

<400> SEQUENCE: 15
guuccauugc uuacuuuuuu uuu                                            23

<210> SEQ ID NO 16
<211> LENGTH: 20
<212> TYPE: DNA
<213> ORGANISM: Artificial Sequence
<220> FEATURE:
<223> OTHER INFORMATION: alpha-tubulin primer

<400> SEQUENCE: 16
ttctccattt acccggcacc                                                20

<210> SEQ ID NO 17
<211> LENGTH: 20
<212> TYPE: DNA
<213> ORGANISM: Artificial Sequence
<220> FEATURE:
<223> OTHER INFORMATION: alpha-tubulin primer

<400> SEQUENCE: 17
gttagtgtag gttgggcgct                                                20

<210> SEQ ID NO 18
<211> LENGTH: 20
<212> TYPE: DNA
<213> ORGANISM: Artificial Sequence
<220> FEATURE:
<223> OTHER INFORMATION: EPB41L5 primer

<400> SEQUENCE: 18
gaaagaaggc ccagcaaacg                                                20
```

<210> SEQ ID NO 19
<211> LENGTH: 20
<212> TYPE: DNA
<213> ORGANISM: Artificial Sequence
<220> FEATURE:
<223> OTHER INFORMATION: EPB41L5 primer

<400> SEQUENCE: 19
agatctcatc ccccaagcct                                               20

<210> SEQ ID NO 20
<211> LENGTH: 20
<212> TYPE: DNA
<213> ORGANISM: Artificial Sequence
<220> FEATURE:
<223> OTHER INFORMATION: PAI-1 primer

<400> SEQUENCE: 20
ccccacttct tcaggctgtt                                               20

<210> SEQ ID NO 21
<211> LENGTH: 20
<212> TYPE: DNA
<213> ORGANISM: Artificial Sequence
<220> FEATURE:
<223> OTHER INFORMATION: PAI-1 primer

<400> SEQUENCE: 21
gccgttgaag tagagggcat                                               20

<210> SEQ ID NO 22
<211> LENGTH: 20
<212> TYPE: DNA
<213> ORGANISM: Artificial Sequence
<220> FEATURE:
<223> OTHER INFORMATION: Slug primer

<400> SEQUENCE: 22
tcatctttgg ggcgagtgag                                               20

<210> SEQ ID NO 23
<211> LENGTH: 20
<212> TYPE: DNA
<213> ORGANISM: Artificial Sequence
<220> FEATURE:
<223> OTHER INFORMATION: Slug primer

<400> SEQUENCE: 23
tgcagctgct tatgtttggc                                               20

<210> SEQ ID NO 24
<211> LENGTH: 20
<212> TYPE: DNA
<213> ORGANISM: Artificial Sequence
<220> FEATURE:
<223> OTHER INFORMATION: ZEB1 primer

<400> SEQUENCE: 24
tatgaatgcc caaactgcaa                                               20

<210> SEQ ID NO 25
<211> LENGTH: 20
<212> TYPE: DNA
<213> ORGANISM: Artificial Sequence
<220> FEATURE:

```
<223> OTHER INFORMATION: ZEB1 primer

<400> SEQUENCE: 25
tggtgatgct gaaagagacg                                               20

<210> SEQ ID NO 26
<211> LENGTH: 20
<212> TYPE: DNA
<213> ORGANISM: Artificial Sequence
<220> FEATURE:
<223> OTHER INFORMATION: Smad4 primer

<400> SEQUENCE: 26
tgcatgactt tgagggacag                                               20

<210> SEQ ID NO 27
<211> LENGTH: 20
<212> TYPE: DNA
<213> ORGANISM: Artificial Sequence
<220> FEATURE:
<223> OTHER INFORMATION: Smad4 primer

<400> SEQUENCE: 27
gtggaagcca caggaatgtt                                               20
```